(12) United States Patent
Yan et al.

(10) Patent No.: US 11,707,527 B2
(45) Date of Patent: Jul. 25, 2023

(54) NANOSCALE DRUG CARRIER CAPABLE OF PASSING THROUGH BLOOD-BRAIN BARRIER

(71) Applicants: KUNSHAN XINYUNDA BIOTECH CO., LTD., Jiangsu (CN); KUNSHAN XINYUNDA BIOTECH CO., LTD. BEIJING BRANCH, Beijing (CN)

(72) Inventors: Xiyun Yan, Beijing (CN); Kelong Fan, Beijing (CN); Meng Zhou, Beijing (CN); Xuehui Chen, Beijing (CN)

(73) Assignees: KUNSHAN XINYUNDA BIOTECH CO., LTD., Jiangsu (CN); KUNSHAN XINYUNDA BIOTECH CO., LTD. BEIJING BRANCH, Beijing (CN)

( * ) Notice: Subject to any disclaimer, the term of this patent is extended or adjusted under 35 U.S.C. 154(b) by 872 days.

(21) Appl. No.: 16/489,302

(22) PCT Filed: Feb. 26, 2018

(86) PCT No.: PCT/CN2018/077295
§ 371 (c)(1),
(2) Date: Aug. 27, 2019

(87) PCT Pub. No.: WO2018/153372
PCT Pub. Date: Aug. 30, 2018

(65) Prior Publication Data
US 2020/0138960 A1    May 7, 2020

(30) Foreign Application Priority Data
Feb. 27, 2017    (CN) .......................... 201710109495.5

(51) Int. Cl.
*A61K 47/42*    (2017.01)
*A61P 35/00*    (2006.01)
(Continued)

(52) U.S. Cl.
CPC ............ *A61K 47/42* (2013.01); *A61K 31/704* (2013.01); *A61K 45/06* (2013.01); *A61P 35/00* (2018.01); *C07K 14/47* (2013.01)

(58) Field of Classification Search
CPC ...... A61K 47/42; A61K 31/704; A61K 45/06; A61P 35/00; C07K 14/47
See application file for complete search history.

(56) References Cited

U.S. PATENT DOCUMENTS 10,195,155 B2 *  2/2019  Yan ........................... A61P 1/04
11,090,391 B2 *  8/2021  Huang .................... A61K 47/64
(Continued)

FOREIGN PATENT DOCUMENTS

CN        104013599 A     9/2014
WO    WO-2012/152222 A1   11/2012
(Continued)

OTHER PUBLICATIONS

PBD-3AJQ_A—PDF generated from NCBI—Apr. 15, 2022 (Year: 2011).*
(Continued)

*Primary Examiner* — Kevin S Orwig
*Assistant Examiner* — John Michael Cronin
(74) *Attorney, Agent, or Firm* — Cooley LLP

(57) ABSTRACT

A nanoscale drug carrier capable of crossing the blood-brain barrier. Said carrier can target brain lesions (brain tumors or other neurodegenerative diseases). The targeting drug carrier capable of crossing the blood-brain barrier comprises all-heavy-chain human ferritin or a functional fragments reconstituted structure or a mutant thereof. The manner for crossing the blood-brain barrier of the drug carrier is receptor-mediated transcytosis. The drug carrier provides an (Continued)

MTTASTQIRQNYHQDSEAAVNRQINLYLQASYTYLSLGFYFDRDDV
ALEGVSHFFRELAEEKREGYERLLKMQNQRGGRIFLQDIKKPDCDE
WGKTPDAMKAAMALEKKLNQALLDLHKLATDKNDPHLCDFLETH
FLDEEVKLIKKMGDHLTNLHRLGGPEAGLGEYLFERLTLKHD effective nanoscale drug carrier for the treatment of brain tumors or other neurodegenerative diseases.

7 Claims, 7 Drawing Sheets

Specification includes a Sequence Listing.

(51) Int. Cl.
*A61K 31/704* (2006.01)
*A61K 45/06* (2006.01)
*C07K 14/47* (2006.01)

(56) References Cited

U.S. PATENT DOCUMENTS

| | | |
|---|---|---|
| 2009/0142360 A1 | 6/2009 | Connor et al. |
| 2015/0037817 A1* | 2/2015 | Yan .................. G01N 33/54326 435/7.8 |

FOREIGN PATENT DOCUMENTS

| | | | |
|---|---|---|---|
| WO | WO-2012/160333 A2 | 11/2012 | |
| WO | WO-2018053434 A1 * | 3/2018 | ........... A61K 31/704 |

OTHER PUBLICATIONS

Fan, Human ferritin for tumor detection and therapy, WIREs Nanomed Nanobiotechnol; 5: 287-298. doi: 10.1002/wnan.1221. (Year: 2013).*

U.S. Pat. No. 11,090,391_SEQ ID No. 1_pep_vs_instant SEQ ID No. 7_ABSS_Alignment; Mar. 1, 2023 from https://abss.uspto.gov/abss4examiners/ (Year: 2023).*

Chain A, Crystal Structure Of Human H Ferritin E140q Mutant. GenBank: 3AJQ_A. Oct. 10, 2012 (Oct. 10, 2012), Comment and Features.

Chain A, Structure Of A48-mer Protein Nanocage Fabricated from Its 24-mer Analogue by Subunit Interface Redesign. GenBank: 5GN8_A. Jan. 25, 2017 (Jan. 25, 2017), Comment and Features.

Mosca et al. (2017). "Use of Ferritin-Based Metal-Encapsulated Nanocarriers as Anti-cancer Agents." Applied Sciences. 7(1), pp. 1-16.

Unnamed Protein Product [*Homo sapiens*], GenBank: BAG54435.1. Jul. 3, 2008 (Jul. 3, 2008), Features.

Santambrogio et al. (1993). "Production and Characterization of Recombinant Hetero-polymers of Human Ferritin H and L Chains." The Journal of Biological Chemistry. 268(17), pp. 12744-12748.

* cited by examiner

A

B

A    B
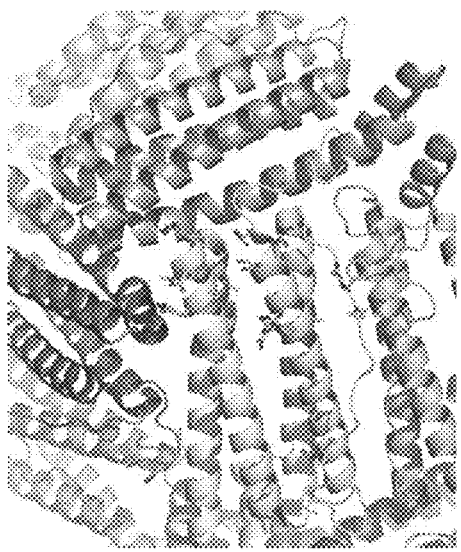 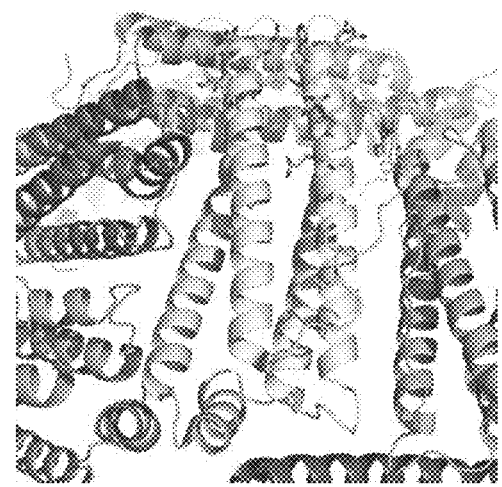
Figure 16
MTTASTQIRQNYHQDSEAAVNRQINLYLQASYTYLSLGFYFDRDDV
ALEGVSHFFRELAEEKREGYERLLKMQNQRGGRIFLQDIKKPDCDE
WGKTPDAMKAAMALEKKLNQALLDLHKLATDKNDPHLCDFLETH
FLDEEVKLIKKMGDHLTNLHRLGGPEAGLGEYLFERLTLKHD
Figure 17

SEQUENCE LISTING

<160> NUMBER OF SEQ ID NOS: 31

<210> SEQ ID NO 1
<211> LENGTH: 44
<212> TYPE: PRT
<213> ORGANISM: Artificial sequence
<220> FEATURE:
<223> OTHER INFORMATION: Functional fragment 1 of human H ferritin

<400> SEQUENCE: 1

Thr Ser Gln Val Arg Gln Asn Tyr His Gln Asp Ser Glu Ala Ala Ile
1               5                   10                  15

Asn Arg Gln Ile Asn Leu Glu Leu Tyr Ala Ser Tyr Val Tyr Leu Ser
            20                  25                  30

Met Ser Tyr Tyr Phe Asp Arg Asp Asp Val Ala Leu
        35                  40

<210> SEQ ID NO 2
<211> LENGTH: 51
<212> TYPE: PRT
<213> ORGANISM: Artificial sequence
<220> FEATURE:
<223> OTHER INFORMATION: Functional fragment 2 of human H ferritin

<400> SEQUENCE: 2

Gly Gly Arg Ile Phe Leu Gln Asp Ile Lys Lys Pro Asp Cys Asp Asp
1               5                   10                  15

Trp Glu Ser Gly Leu Asn Ala Met Glu Cys Ala Leu His Leu Glu Lys
            20                  25                  30

Asn Val Asn Gln Ser Leu Leu Glu Leu His Lys Leu Ala Thr Asp Lys
        35                  40                  45

Asn Asp Pro
    50

<210> SEQ ID NO 3
<211> LENGTH: 19
<212> TYPE: PRT
<213> ORGANISM: Artificial sequence
<220> FEATURE:
<223> OTHER INFORMATION: Functional fragment 3 of human H ferritin

<400> SEQUENCE: 3

Gly Asp His Val Thr Asn Leu Arg Lys Met Gly Ala Pro Glu Ser Gly
1               5                   10                  15

Leu Ala Glu

<210> SEQ ID NO 4
<211> LENGTH: 28
<212> TYPE: PRT
<213> ORGANISM: Artificial sequence
<220> FEATURE:
<223> OTHER INFORMATION: scaffold sequence1

<400> SEQUENCE: 4

Glu Gly Val Ser His Phe Phe Arg Glu Leu Ala Glu Glu Lys Arg Glu
1               5                   10                  15

Gly Tyr Glu Arg Leu Leu Lys Met Gln Asn Gln Arg
            20                  25

<210> SEQ ID NO 5
<211> LENGTH: 21
<212> TYPE: PRT
<213> ORGANISM: Artificial sequence

```
<220> FEATURE:
<223> OTHER INFORMATION: scaffold sequence2

<400> SEQUENCE: 5

His Leu Cys Asp Phe Leu Glu Thr His Phe Leu Asp Glu Glu Val Lys
1               5                   10                  15

Leu Ile Lys Lys Met
            20

<210> SEQ ID NO 6
<211> LENGTH: 11
<212> TYPE: PRT
<213> ORGANISM: Artificial sequence
<220> FEATURE:
<223> OTHER INFORMATION: scaffold sequence3

<400> SEQUENCE: 6

Tyr Leu Phe Glu Arg Leu Thr Leu Lys His Asp
1               5                   10

<210> SEQ ID NO 7
<211> LENGTH: 175
<212> TYPE: PRT
<213> ORGANISM: Artificial sequence
<220> FEATURE:
<223> OTHER INFORMATION: chimeric human H ferritin

<400> SEQUENCE: 7

Met Thr Ser Gln Val Arg Gln Asn Tyr His Gln Asp Ser Glu Ala Ala
1               5                   10                  15

Ile Asn Arg Gln Ile Asn Leu Glu Leu Tyr Ala Ser Tyr Val Tyr Leu
            20                  25                  30

Ser Met Ser Tyr Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ile Phe Leu Gln
65                  70                  75                  80

Asp Ile Lys Lys Pro Asp Cys Asp Asp Trp Glu Ser Gly Leu Asn Ala
                85                  90                  95

Met Glu Cys Ala Leu His Leu Glu Lys Asn Val Asn Gln Ser Leu Leu
            100                 105                 110

Glu Leu His Lys Leu Ala Thr Asp Lys Asn Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Val Thr Asn Leu Arg Lys Met Gly Ala Pro Glu Ser
145                 150                 155                 160

Gly Leu Ala Glu Tyr Leu Phe Glu Arg Leu Thr Leu Lys His Asp
                165                 170                 175

<210> SEQ ID NO 8
<211> LENGTH: 183
<212> TYPE: PRT
<213> ORGANISM: Artificial sequence
<220> FEATURE:
<223> OTHER INFORMATION: mutant 1

<400> SEQUENCE: 8

Met Thr Thr Ala Ser Thr Ser Gln Val Arg Gln Asn Tyr His Gln Asp
1               5                   10                  15
```

Ser Glu Ala Ala Ile Asn Arg Gln Ile Asn Leu Glu Leu Tyr Ala Ser
            20                  25                  30

Tyr Val Tyr Leu Ser Met Ser Tyr Phe Asp Arg Asp Val Ala
        35                  40                  45

Leu Lys Asn Phe Ala Lys Tyr Phe Leu His Gln Ser His Glu Lys Arg
 50                  55                  60

Glu Gly Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
                    100                 105                 110

Gln Ser Leu Leu Glu Leu His Lys Leu Ala Thr Asp Lys Asn Asp Pro
                115                 120                 125

His Leu Cys Asp Phe Ile Glu Thr His Tyr Leu Asn Glu Gln Val Lys
            130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                    165                 170                 175

Gly Asp Ser Asp Asn Glu Ser
            180

<210> SEQ ID NO 9
<211> LENGTH: 183
<212> TYPE: PRT
<213> ORGANISM: Artificial sequence
<220> FEATURE:
<223> OTHER INFORMATION: mutant 2

<400> SEQUENCE: 9

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Phe Asp Arg Asp Val Ala
        35                  40                  45

Leu Lys Asn Phe Ala Lys Tyr Phe Leu His Gln Ser His Glu Glu Arg
 50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
                    100                 105                 110

Gln Ser Leu Leu Glu Leu His Lys Leu Ala Thr Asp Lys Asn Asp Pro
                115                 120                 125

His Leu Cys Asp Phe Ile Ala Thr His Tyr Leu Asn Glu Gln Val Lys
            130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                    165                 170                 175

Gly Asp Ser Asp Asn Glu Ser
            180

```
<210> SEQ ID NO 10
<211> LENGTH: 183
<212> TYPE: PRT
<213> ORGANISM: Artificial sequence
<220> FEATURE:
<223> OTHER INFORMATION: human H ferritin

<400> SEQUENCE: 10

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
            85                  90                  95

Gly Leu Asn Ala Met Glu Cys Ala Leu His Leu Glu Lys Asn Val Asn
        100                 105                 110

Gln Ser Leu Leu Glu Leu His Lys Leu Ala Thr Asp Lys Asn Asp Pro
    115                 120                 125

His Leu Cys Asp Phe Ile Glu Thr His Tyr Leu Asn Glu Gln Val Lys
130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 11
<211> LENGTH: 114
<212> TYPE: PRT
<213> ORGANISM: Artificial sequence
<220> FEATURE:
<223> OTHER INFORMATION: Fusion form of SEQ ID NO:3, 2 and 1

<400> SEQUENCE: 11

Thr Ser Gln Val Arg Gln Asn Tyr His Gln Asp Ser Glu Ala Ala Ile
1               5                   10                  15

Asn Arg Gln Ile Asn Leu Glu Leu Tyr Ala Ser Tyr Val Tyr Leu Ser
            20                  25                  30

Met Ser Tyr Tyr Phe Asp Arg Asp Asp Val Ala Leu Gly Gly Arg Ile
        35                  40                  45

Phe Leu Gln Asp Ile Lys Lys Pro Asp Cys Asp Asp Trp Glu Ser Gly
    50                  55                  60

Leu Asn Ala Met Glu Cys Ala Leu His Leu Glu Lys Asn Val Asn Gln
65                  70                  75                  80

Ser Leu Leu Glu Leu His Lys Leu Ala Thr Asp Lys Asn Asp Pro Gly
                85                  90                  95

Asp His Val Thr Asn Leu Arg Lys Met Gly Ala Pro Glu Ser Gly Leu
            100                 105                 110

Ala Glu
```

<210> SEQ ID NO 12
<211> LENGTH: 175
<212> TYPE: PRT
<213> ORGANISM: homo sapiens

<400> SEQUENCE: 12

```
Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175
```

<210> SEQ ID NO 13
<211> LENGTH: 175
<212> TYPE: PRT
<213> ORGANISM: Artificial sequence
<220> FEATURE:
<223> OTHER INFORMATION: N-loop

<400> SEQUENCE: 13

```
Met Ser Ser Gln Ile Arg Gln Asn Tyr His Gln Asp Ser Glu Ala Ala
1               5                   10                  15

Val Asn Arg Gln Ile Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ile Phe Leu Gln
65                  70                  75                  80

Asp Ile Lys Lys Pro Asp Cys Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Lys Leu Ala Thr Asp Lys Asn Asp Pro His Leu Cys Asp
        115                 120                 125

Phe Leu Glu Thr His Phe Leu Asp Glu Glu Val Lys Leu Ile Lys Lys
    130                 135                 140
```

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
            165                 170                 175

<210> SEQ ID NO 14
<211> LENGTH: 175
<212> TYPE: PRT
<213> ORGANISM: Artificial sequence
<220> FEATURE:
<223> OTHER INFORMATION: C-loop

<400> SEQUENCE: 14

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Asp Cys Asp Glu Trp Glu Ser Gly Leu Asn Ala
                85                  90                  95

Met Glu Cys Ala Leu His Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu Arg Lys Met Gly Ala Pro Glu Ala
145                 150                 155                 160

Gly Leu Gly Glu Tyr Leu Phe Glu Arg Leu Thr Leu Lys His Asp
            165                 170                 175

<210> SEQ ID NO 15
<211> LENGTH: 175
<212> TYPE: PRT
<213> ORGANISM: Artificial sequence
<220> FEATURE:
<223> OTHER INFORMATION: NC-loop

<400> SEQUENCE: 15

Met Ser Ser Gln Ile Arg Gln Asn Tyr His Gln Asp Ser Glu Ala Ala
1               5                   10                  15

Val Asn Arg Gln Ile Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ile Phe Leu Gln
65                  70                  75                  80

Asp Ile Lys Lys Pro Asp Cys Asp Glu Trp Glu Ser Gly Leu Asn Ala
                85                  90                  95

Met Glu Cys Ala Leu His Leu Glu Lys Lys Leu Asn Gln Ala Leu Leu
            100                 105                 110

```
Asp Leu His Lys Leu Ala Thr Asp Lys Asn Asp Pro His Leu Cys Asp
            115                 120                 125

Phe Leu Glu Thr His Phe Leu Asp Glu Glu Val Lys Leu Ile Lys Lys
        130                 135                 140

Met Gly Asp His Leu Thr Asn Leu Arg Lys Met Gly Ala Pro Glu Ala
145                 150                 155                 160

Gly Leu Gly Glu Tyr Leu Phe Glu Arg Leu Thr Leu Lys His Asp
                165                 170                 175

<210> SEQ ID NO 16
<211> LENGTH: 175
<212> TYPE: PRT
<213> ORGANISM: Artificial sequence
<220> FEATURE:
<223> OTHER INFORMATION: N-terminal

<400> SEQUENCE: 16

Met Ser Ser Gln Ile Arg Gln Asn Tyr His Gln Asp Ser Glu Ala Ala
1               5                   10                  15

Val Asn Arg Gln Ile Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ile Phe Leu Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Lys Leu Ala Thr Asp Lys Asn Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175

<210> SEQ ID NO 17
<211> LENGTH: 175
<212> TYPE: PRT
<213> ORGANISM: Artificial sequence
<220> FEATURE:
<223> OTHER INFORMATION: C-terminal

<400> SEQUENCE: 17

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
```

```
                65                  70                  75                  80
Asp Ile Lys Lys Pro Ala Glu Asp Glu Trp Glu Ser Gly Leu Asn Ala
                85                  90                  95

Met Glu Cys Ala Leu His Leu Glu Lys Lys Leu Asn Gln Ala Leu Leu
                100                 105                 110

Asp Leu His Ala Leu Gly Ser Ala Arg Thr Asp Pro His Leu Cys Asp
                115                 120                 125

Phe Leu Glu Thr His Phe Leu Asp Glu Glu Val Lys Leu Ile Lys Lys
                130                 135                 140

Met Gly Asp His Leu Thr Asn Leu Arg Lys Met Gly Ala Pro Glu Ala
145                 150                 155                 160

Gly Leu Gly Glu Tyr Leu Phe Glu Arg Leu Thr Leu Lys His Asp
                165                 170                 175

<210> SEQ ID NO 18
<211> LENGTH: 175
<212> TYPE: PRT
<213> ORGANISM: Artificial sequence
<220> FEATURE:
<223> OTHER INFORMATION: NC fusion

<400> SEQUENCE: 18

Met Ser Ser Gln Ile Arg Gln Asn Tyr His Gln Asp Ser Glu Ala Ala
1               5                   10                  15

Val Asn Arg Gln Ile Asn Leu Tyr Leu Gln Ala Ser Tyr Thr Tyr Leu
                20                  25                  30

Ser Leu Gly Phe Tyr Phe Asp Arg Asp Asp Val Ala Leu Glu Gly Val
            35                  40                  45

Ser His Phe Phe Arg Glu Leu Ala Glu Glu Lys Arg Glu Gly Tyr Glu
        50                  55                  60

Arg Leu Leu Lys Met Gln Asn Gln Arg Gly Gly Arg Ile Phe Leu Gln
65                  70                  75                  80

Asp Ile Lys Lys Pro Ala Glu Asp Glu Trp Glu Ser Gly Leu Asn Ala
                85                  90                  95

Met Glu Cys Ala Leu His Leu Glu Lys Lys Leu Asn Gln Ala Leu Leu
                100                 105                 110

Asp Leu His Lys Leu Ala Thr Asp Lys Asn Asp Pro His Leu Cys Asp
                115                 120                 125

Phe Leu Glu Thr His Phe Leu Asp Glu Glu Val Lys Leu Ile Lys Lys
                130                 135                 140

Met Gly Asp His Leu Thr Asn Leu Arg Lys Met Gly Ala Pro Glu Ala
145                 150                 155                 160

Gly Leu Gly Glu Tyr Leu Phe Glu Arg Leu Thr Leu Lys His Asp
                165                 170                 175

<210> SEQ ID NO 19
<211> LENGTH: 178
<212> TYPE: PRT
<213> ORGANISM: Artificial sequence
<220> FEATURE:
<223> OTHER INFORMATION: chimric human ferritin

<400> SEQUENCE: 19

Met Thr Thr Ala Ser Thr Gln Ile Arg Gln Asn Tyr His Gln Asp Ser
1               5                   10                  15

Glu Ala Ala Val Asn Arg Gln Ile Asn Leu Tyr Leu Gln Ala Ser Tyr
                20                  25                  30
```

```
Thr Tyr Leu Ser Leu Gly Phe Tyr Phe Asp Arg Asp Val Ala Leu
            35                  40                  45

Glu Gly Val Ser His Phe Phe Arg Glu Leu Ala Glu Glu Lys Arg Glu
 50                  55                  60

Gly Tyr Glu Arg Leu Leu Lys Met Gln Asn Gln Arg Gly Gly Arg Ile
 65                  70                  75                  80

Phe Leu Gln Asp Ile Lys Lys Pro Asp Cys Asp Glu Trp Gly Lys Thr
                 85                  90                  95

Pro Asp Ala Met Lys Ala Ala Met Ala Leu Glu Lys Lys Leu Asn Gln
             100                 105                 110

Ala Leu Leu Asp Leu His Lys Leu Ala Thr Asp Lys Asn Asp Pro His
             115                 120                 125

Leu Cys Asp Phe Leu Glu Thr His Phe Leu Asp Glu Glu Val Lys Leu
130                 135                 140

Ile Lys Lys Met Gly Asp His Leu Thr Asn Leu His Arg Leu Gly Gly
145                 150                 155                 160

Pro Glu Ala Gly Leu Gly Glu Tyr Leu Phe Glu Arg Leu Thr Leu Lys
                 165                 170                 175

His Asp

<210> SEQ ID NO 20
<211> LENGTH: 5
<212> TYPE: PRT
<213> ORGANISM: Artificial sequence
<220> FEATURE:
<223> OTHER INFORMATION: sequence of important residues

<400> SEQUENCE: 20

Thr Thr Ala Ser Thr
1               5

<210> SEQ ID NO 21
<211> LENGTH: 4
<212> TYPE: PRT
<213> ORGANISM: Artificial sequence
<220> FEATURE:
<223> OTHER INFORMATION: sequence of important residues

<400> SEQUENCE: 21

His Gln Asp Ser
1

<210> SEQ ID NO 22
<211> LENGTH: 3
<212> TYPE: PRT
<213> ORGANISM: Artificial sequence
<220> FEATURE:
<223> OTHER INFORMATION: sequence of important residues

<400> SEQUENCE: 22

Arg Gln Ile
1

<210> SEQ ID NO 23
<211> LENGTH: 3
<212> TYPE: PRT
<213> ORGANISM: Artificial sequence
<220> FEATURE:
<223> OTHER INFORMATION: sequence of important residues

<400> SEQUENCE: 23

Ile Phe Leu
```

-continued

```
<210> SEQ ID NO 24
<211> LENGTH: 2
<212> TYPE: PRT
<213> ORGANISM: Artificial sequence
<220> FEATURE:
<223> OTHER INFORMATION: sequence of important residues

<400> SEQUENCE: 24

Asp Cys
1

<210> SEQ ID NO 25
<211> LENGTH: 7
<212> TYPE: PRT
<213> ORGANISM: Artificial sequence
<220> FEATURE:
<223> OTHER INFORMATION: sequence of important residues

<400> SEQUENCE: 25

Lys Leu Ala Thr Asp Lys Asn
1               5

<210> SEQ ID NO 26
<211> LENGTH: 6
<212> TYPE: PRT
<213> ORGANISM: Artificial sequence
<220> FEATURE:
<223> OTHER INFORMATION: scaffold sequence

<400> SEQUENCE: 26

Gln Ile Arg Gln Asn Tyr
1               5

<210> SEQ ID NO 27
<211> LENGTH: 5
<212> TYPE: PRT
<213> ORGANISM: Artificial sequence
<220> FEATURE:
<223> OTHER INFORMATION: scaffold sequence

<400> SEQUENCE: 27

Glu Ala Ala Val Asn
1               5

<210> SEQ ID NO 28
<211> LENGTH: 55
<212> TYPE: PRT
<213> ORGANISM: Artificial sequence
<220> FEATURE:
<223> OTHER INFORMATION: scaffold sequence

<400> SEQUENCE: 28

Asn Leu Tyr Leu Gln Ala Ser Tyr Thr Tyr Leu Ser Leu Gly Phe Tyr
1               5                   10                  15

Phe Asp Arg Asp Asp Val Ala Leu Glu Gly Val Ser His Phe Phe Arg
            20                  25                  30

Glu Leu Ala Glu Glu Lys Arg Glu Gly Tyr Glu Arg Leu Leu Lys Met
        35                  40                  45

Gln Asn Gln Arg Gly Gly Arg
    50                  55

<210> SEQ ID NO 29
<211> LENGTH: 6
```

```
<212> TYPE: PRT
<213> ORGANISM: Artificial sequence
<220> FEATURE:
<223> OTHER INFORMATION: scaffold sequence

<400> SEQUENCE: 29

Gln Asp Ile Lys Lys Pro
1               5

<210> SEQ ID NO 30
<211> LENGTH: 28
<212> TYPE: PRT
<213> ORGANISM: Artificial sequence
<220> FEATURE:
<223> OTHER INFORMATION: scaffold sequence

<400> SEQUENCE: 30

Asp Glu Trp Gly Lys Thr Pro Asp Ala Met Lys Ala Ala Met Ala Leu
1               5                   10                  15

Glu Lys Lys Leu Asn Gln Ala Leu Leu Asp Leu His
            20                  25

<210> SEQ ID NO 31
<211> LENGTH: 53
<212> TYPE: PRT
<213> ORGANISM: Artificial sequence
<220> FEATURE:
<223> OTHER INFORMATION: scaffold sequence

<400> SEQUENCE: 31

Asp Pro His Leu Cys Asp Phe Leu Glu Thr His Phe Leu Asp Glu Glu
1               5                   10                  15

Val Lys Leu Ile Lys Lys Met Gly Asp His Leu Thr Asn Leu His Arg
            20                  25                  30

Leu Gly Gly Pro Glu Ala Gly Leu Gly Glu Tyr Leu Phe Glu Arg Leu
        35                  40                  45

Thr Leu Lys His Asp
    50
```

NANOSCALE DRUG CARRIER CAPABLE OF PASSING THROUGH BLOOD-BRAIN BARRIER

CROSS-REFERENCE TO RELATED APPLICATIONS

This application is a 371 U.S. national phase application of International Patent Application No. PCT/CN2018/077295, filed on Feb. 26, 2018, which claims priority to Chinese Patent Application No. 201710109495.5, filed on Feb. 27, 2017, the contents of each of which are hereby incorporated in their entirety.

TECHNICAL FIELD

The invention belongs to the field of nano-biology, biomimicry and biomedicine. Particularly, the invention relates to a nanoscale drug delivery system capable of crossing the blood brain barrier and having an ability of actively targeting brain lesions; and the delivery system includes an all-heavy-chain human ferritin or a structure reconstituted from the functional fragments thereof or a mutant thereof.

REFERENCE TO SEQUENCE LISTING

This application is being filed electronically via EFS-Web and includes an electronically submitted sequence listing in .txt format. The .txt file contains a sequence listing entitled NTDU-001_00US_SeqList.txt created on Jan. 21, 2020, and having a size of 25,955 bytes. The sequence listing contained in this .txt file is part of the specification and is incorporated herein by reference in its entirety.

BACKGROUND

Blood-Brain Barrier (BBB for short) is an international problem to the treatment of brain diseases. Due to the existence of BBB, 100% macromolecule drugs and more than 90% small molecule drugs cannot cross it and reach brain tissues, which extremely limits efficacy of drugs to brain diseases[1-3]. Therefore, a drug capable of crossing BBB effectively has been highly expected.

BBB is a kind of special structure formed mainly by closely linked brain capillary endothelial cells, astrocyte sticky ends and perithelial cells. Under a normal physiological condition, BBB only allows gas and small liposoluble molecules (MW less than 600 Da) to cross[4]. There are two ways for exogenous substances to cross BBB, namely free diffusion and receptor-mediated active transport. Free diffusion is limited to low molecular-weight, non-polar and lipophilic substances, while most of pharmaceutical molecules cross BBB mainly via a receptor-mediated transport system on brain endothelial cells[4]. Therefore, the key for designing a drug capable of crossing BBB is to discover and identify a receptor on the blood brain barrier having transcytosis activity, as well as a targeting carrier that bind to the receptor.

SUMMARY OF THE INVENTION

A first aspect of the invention relates to a functional fragment of human H-ferritin, wherein the functional fragment is shorter than the full-length human H-ferritin, and is capable of forming a cage protein comprising a plurality of subunits after being reconstituted, and the functional fragment is presented on the outer surface of the cage protein, wherein the full-length human H-ferritin has a sequence as shown in SEQ ID NO: 10, preferably, the functional fragment has a sequence as shown in SEQ ID NO: 1-3, 20-25, or has a sequence with at least 85% sequence identity to the sequence as shown in any one of SEQ ID NO: 1-3, 20-25 and is capable of being presented on the outer surface of the cage protein after being reconstituted to form the cage protein, or has a sequence having one or more amino acid residue substitution, deletion and/or addition in the sequence as shown in any one of SEQ ID NO: 1-3, 20-25 and is capable of being presented on the outer surface of the cage protein after being reconstituted to form the cage protein; and/or preferably, when reconstituted, the sequence among the functional fragment is a scaffold sequence, which is an amino acid sequence region of human ferritin L subunit corresponding to the region in human ferritin H subunit, and preferably, the scaffold sequence is selected from SEQ ID No. 4-6, 26-31.

A second aspect of the invention relates to a cage protein, wherein the cage protein comprises a plurality of subunits self-assembled into the cage protein, wherein the portion of each subunit that is presented on the surface of the cage protein is the functional fragment of human H-ferritin according to claim 1, preferably, the subunit has a sequence as shown in SEQ ID No. 7 or 19; and/or, the plurality of subunits are H subunits and L subunits of human ferritin, and self-assembled into a cage protein of hybrid human ferritin, in which the ratio of H and L subunits is different from the ratio of the H and L subunits in a natural human ferritin, and the bioactivity of human ferritin is maintained, preferably, the ratio of H/L subunits is 1:23~23:1.

A third aspect of the invention relates to a human H-ferritin mutant, which has one or more amino acid residue mutation compared with all-H human ferritin, preferably, the mutation is located inside the human H-ferritin or on the outer surface the human H-ferritin, preferably, the mutation is located in the scaffold sequence as shown in SEQ ID No. 4-6 and 26-31, and the mutant recognizes its natural receptor TfR1 and is transported by TfR1 to cross BBB, preferably, the human H-ferritin mutant has a sequence as shown in SEQ ID NO: 8 or 9, or has a sequence having 85% sequence identity to the sequence as shown in SEQ ID NO: 8 or 9 and is capable of forming a cage protein comprising a plurality of subunits, or has a sequence having one or more amino acid residue substitution, deletion and/or addition in the sequence as shown in SEQ ID NO: 8 or 9 and is capable of forming a cage protein comprising a plurality of subunits; and/or the functional fragments of the human H-ferritin mutant replace the outer surface regions of human L-ferritin, preferably, the functional fragments of the human H-ferritin mutant replace regions of amino acid positions 10-13, 19-21, 77-79, 86-87, 91-102, 116-122, 153-157 of a human L-ferritin having a sequence as shown in SEQ ID No. 12, or replace amino acid sequences in a human L-ferritin having a sequence as shown in SEQ ID No. 12 corresponding to amino acid sequences as shown in SEQ ID No. 20-25

In some embodiments, the cage protein has an ability to cross the blood brain barrier.

In some embodiments, said a plurality of subunits comprises 3-30, preferably 6-28, more preferably 8-26, and most preferably 24 subunits.

In some embodiments, the cage protein comprises a drug, preferably, the drug is a chemotherapeutic drug or a drug against neurodegenerative diseases, preferably, the drug is selected from alkylating agents, e.g., cisplatin and carboplatin and derivatives thereof; antibiotics, e.g., doxorubicin, daunomycin, daunorubicin; plant alkaloids, e.g. vinblastine;

radiopharmaceuticals, e.g., $^{64}$Cu, $^{235}$U; neurotransmitters, e.g., carbachol, atropine, scopolamine, dopamine and derivatives thereof; dopamine receptor agonists, e.g., bromocriptine, pergolide, apomorphine and other ergot alkaloid derivatives and non-ergot alkaloid derivatives; central nervous anticholinergic agents, e.g., trihexyphenidyl, benzatropine and procyclidine; cholinoceptor agonists, e.g., muscarine, pilocarpine; γ-secretase inhibitors, e.g., difluoro ketones; antioxidants, e.g., melatonin; anesthetics, e.g., anthryl amine.

A fourth aspect of the invention relates to a pharmaceutical composition, comprising the functional fragment or the cage protein or the human H-ferritin mutant mentioned above.

In some embodiments, the functional fragment or the cage protein or the human H-ferritin mutant or the pharmaceutical composition mentioned above are used for preparation of a drug carrier.

A fifth aspect of the invention relates to use of the functional fragment or the cage protein or the human H-ferritin mutant or the pharmaceutical composition mentioned above in preparation of a drug carrier for treating or preventing a disease.

A sixth aspect of the invention relates to use of human H-ferritin or the functional fragment or the cage protein or the human H-ferritin mutant or the pharmaceutical composition mentioned above in preparation of a blood brain barrier-crossing drug carrier for treating or preventing a disease, preferably, the drug carrier also targets a brain lesion or disease.

A seventh aspect of the invention relates to a method for treating and/or preventing a disease, including a step of administering the functional fragment or the cage protein or the human H-ferritin mutant or the pharmaceutical composition mentioned above to a subject.

An eighth aspect of the invention relates to a method for treating and/or preventing a brain disease, including a step of administering human H-ferritin or the functional fragment or the cage protein or the human H-ferritin mutant or the pharmaceutical composition mentioned above to a subject.

In some embodiments, the drug is selected from alkylating agents, e.g., nitrosoureas; Pt types, e.g., cisplatin and carboplatin and derivatives thereof; antimetabolites, e.g., thymidylate synthase inhibitors; antibiotics, e.g., doxorubicin, daunomycin, daunorubicin; natural extracts, e.g., plant alkaloids (vinblastine); hormones, e.g., anti-estrogens (tamoxifen); radiopharmaceuticals, e.g., $^{64}$Cu, $^{235}$U; neurotransmitters, e.g., carbachol, atropine, scopolamine, dopamine and derivatives thereof; dopamine receptor agonists, e.g., bromocriptine, pergolide, apomorphine and other ergot alkaloid derivatives and non-ergot alkaloid derivatives; central nervous anticholinergic agents, e.g., trihexyphenidyl, benzatropine and procyclidine; cholinoceptor agonists, e.g., muscarine, pilocarpine; γ-secretase inhibitors, e.g., difluoro ketones; antioxidants, e.g., melatonin; anesthetics, e.g., anthryl amine; and/or the disease is selected from a brain tumor, Alzheimer's disease, Parkinson's disease, stroke, epilepsy, Huntington's disease and amyotrophic lateral sclerosis, and/or human malignant tumor and cancer, preferably, the drug is used for rectal cancer, lung cancer, breast cancer, ovarian cancer, melanoma, stomach cancer, pancreatic cancer, bladder cancer, kidney cancer, prostatic cancer and various hematologic malignancies, e.g., Hodgkin's disease, Non-Hodgkin's lymphoma, leukemia, etc.

In some embodiments, the brain disease is selected from a brain tumor, Alzheimer's disease, Parkinson's disease, stroke, epilepsy, Huntington's disease and amyotrophic lateral sclerosis.

In other words, on the basis of systematically studying BBB structures and functional features, the inventors have biomimetically synthesized a novel ferritin nanoscale-drug carrier from a new perspective according to the unique shell-core structure of natural human ferritin (Kelong Fan, et al and Xiyun Yan. Magnetoferritin nanoparticles for targeting and visualizing tumour tissues. Nature Nanotechnol. 7, 459-464 (2012).); PCT patent application: PCT/CN2012/075291). The carrier has the following features: the carrier is a 24-polymer cage protein self-assembled by H subunits of human ferritin (called human H-ferritin); the diameter of the cage protein shell is 12 nm and the diameter of the cavity thereof is 8 nm. The diameter of the shell and cavity may increase or decrease accordingly based on number of the H subunits forming the cage protein. The inventors' preliminary work has proved that such ferritin nanoparticle has dual functions, namely, capable of specifically targeting a tumor and effectively carrying a chemotherapeutic drug to reach the tumor site accurately, thus inhibiting tumor's growth and metastasis (Minmin Liang, Kelong Fan, et al and Xiyun Yan. H-ferritin-nanocaged doxorubicin nanoparticles specifically target and kill tumors with a single-dose injection. Proc. Natl. Acad. Sci. USA 111(41): 14900-14905 (2014); Chinese patent application: 201410230829.0). In the present invention, it has been found by the inventor that the cage protein formed by human H-ferritin can cross the blood brain barrier via TfR1-mediated transcytosis by binding to a natural Transferrin Receptor 1 (TfR1) on BBB brain endothelial cells, without any label and modification. Meanwhile, human H-ferritin per se has an ability of targeting tumor cells, therefore human H-ferritin can not only cross the blood brain barrier, but can also achieve active brain lesion targeting. It has also been found by the inventor that when the cage protein formed by human H-ferritin binds to TfR1 for crossing BBB, the amino acid sequences presented on the outer surface of the shell of human H-ferritin, in particular the sequences as shown in SEQ ID NO: 1-3, are the key of binding and BBB crossing. In addition, as long as subunits comprising the sequences as shown in SEQ ID NO: 1-3 self-assemble into a cage protein and the sequences are presented on the outer surface, TfR1 binding and BBB effective crossing may be achieved.

In some embodiments, the invention relates to the following items:

1. A nanoscale-drug carrier capable of crossing blood brain barrier, wherein the carrier comprises an all-heavy-chain human ferritin.

2. Use of an all-heavy-chain human ferritin or functional fragment thereof in preparation of a drug carrier for crossing blood brain barrier.

3. Use of an all-heavy-chain human ferritin or functional fragment thereof in preparation of a drug carrier for crossing blood brain barrier and targeting a brain lesion or disease.

4. The use according to 2 or 3, wherein the drug carrier carries a drug ingredient, and the drug ingredient is preferably a chemotherapeutic drug against a brain tumor, preferably doxorubicin; or a drug against a neurodegenerative disease, preferably donepezil or L-dopamine.

5. A pharmaceutical composition capable of crossing blood brain barrier, wherein the pharmaceutical composition comprises the carrier of 1 and a drug ingredient for treating a brain lesion or disease, and the drug ingredient is preferably a chemotherapeutic drug against a brain tumor, preferably doxorubicin; or a drug against a neurodegenerative disease, preferably donepezil or L-dopamine.

6. The use according to 3 or the pharmaceutical composition according to 4, wherein the brain lesion or disease includes a brain tumor or neurodegenerative disease, and the brain tumor is preferably glioma, and the neurodegenerative disease is preferably Alzheimer's disease or Parkinson's disease.

7. The use according to 2 or 3, wherein the all-heavy-chain human ferritin crosses the blood brain barrier via a receptor-mediated transcytosis, and the receptor is preferably TfR1.

8. The carrier according to 1, wherein the all-heavy-chain human ferritin is a cage protein having a cavity and is formed by self-assemble of human ferritin H subunits or mutants thereof, and the cavity can be used for loading a drug ingredient.

9. The carrier according to claim 8, wherein the outer surface of the cage protein binds to the receptor TfR1, and the mutation is located on an inner surface of the cage protein.

10. The carrier according to claim 8, wherein the mutant does not affect the binding of the all-heavy-chain human H-ferritin to the receptor, and maintains the cavity structure.

The targeting drug carrier of the invention comprises an all-heavy-chain human ferritin or a structure reconstituted from the functional fragments thereof or a mutant thereof, and crosses the blood brain barrier via receptor-mediated transcytosis. The nanoscale-drug carrier of the invention is expected to be an effective nanoscale-drug carrier for the treatment of diseases, in particular brain tumors or neurodegenerative diseases.

(A) A schematic diagram of BBB in vitro;
(B) A comparison between transcytosis of human H-ferritin and non-specific BSA crossing.

Figure 6:
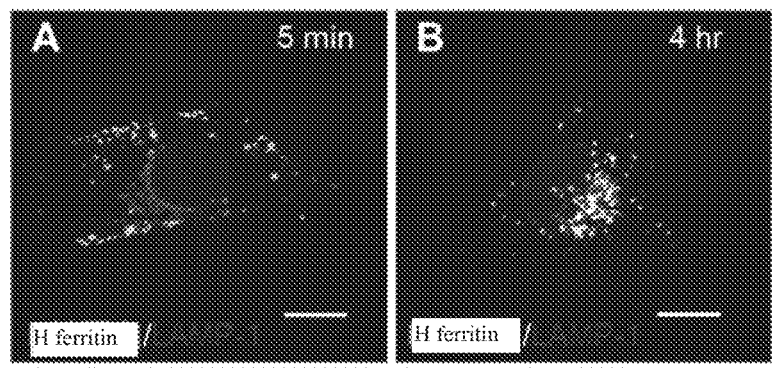

FIG. 6 shows that human H-ferritins will enter the cells via receptor TfR1-mediated endocytosis after binding with human glioma cells U-87 MG (A), and then enter the lysosomes (B). By this way, H-ferritins may be effectively enriched in glioma cells and release the drug as loaded by a lysosome pathway.

Figure 7:
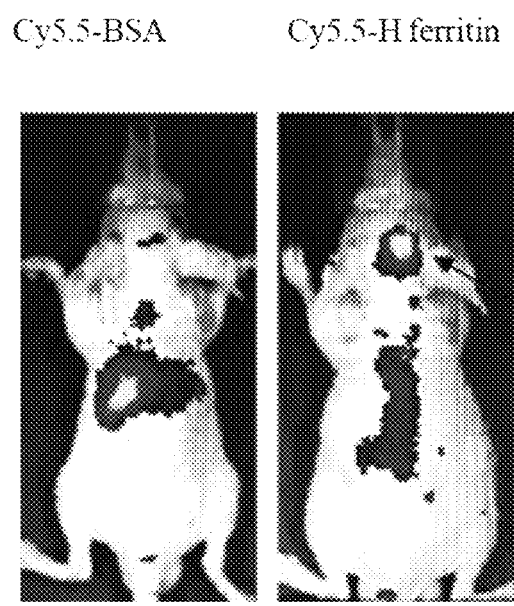

FIG. 7 shows that a glioma lesion may be specifically targeted by human H-ferritin in vivo, and the direction of an arrow is the glioma lesion.

Figure 8:
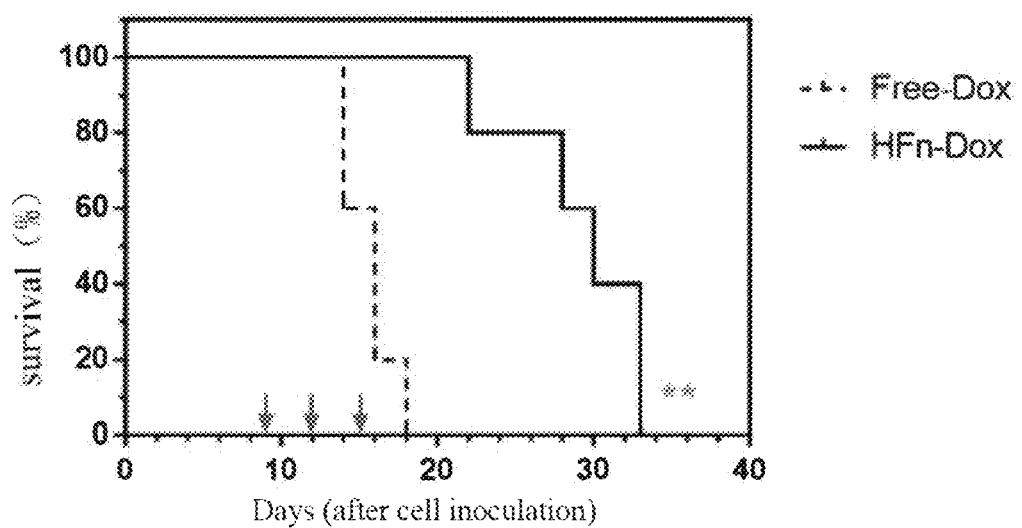

FIG. 8 shows that H-ferritin loading with doxorubicin is capable of significantly improving survival time of a glioma mouse model. Compared with the free doxorubicin (Free-Dox) group, the survival time is prolonged significantly, **p<0.01. The arrow shows administration time. Mean survival time of the Free-Dox group is 15d and the HFn-Dox group is 30d.

Figure 9:
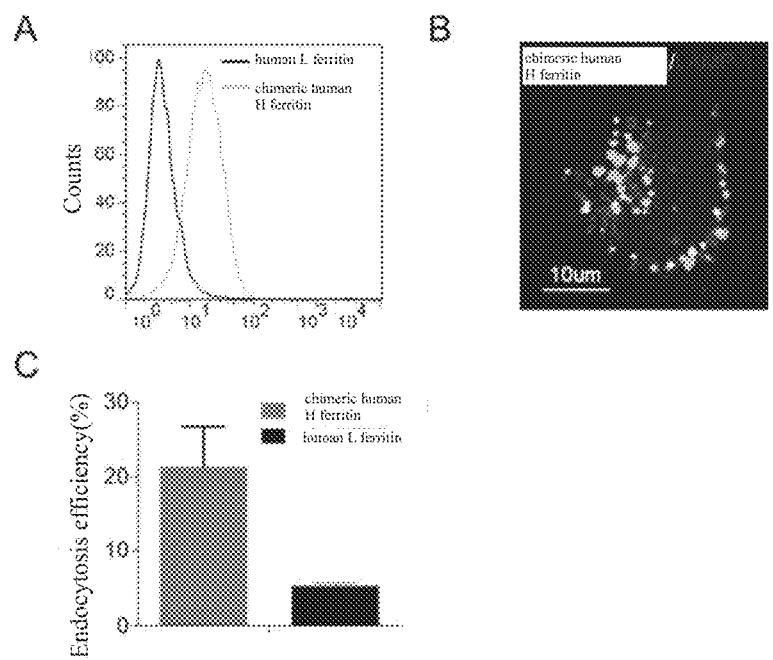

FIG. 9 shows that chimeric human H-ferritins can still achieve specific binding with human brain endothelial cells (A), do not enter the lysosomes in human brain endothelial cells (B), and cross an in vitro BBB model effectively (C).

Figure 10:
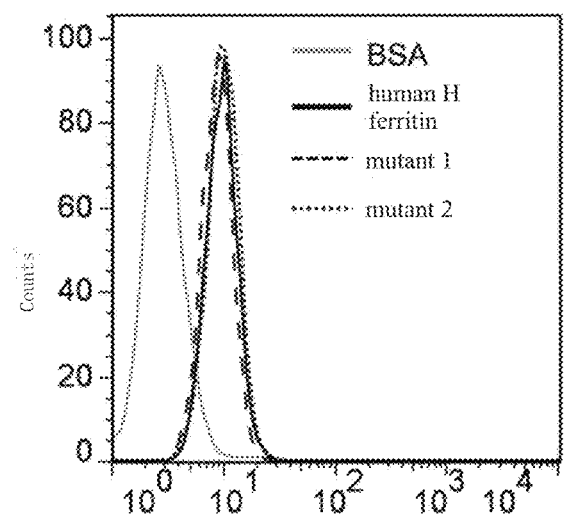

FIG. 10 shows that the specific binding between mutants of human H-ferritin with internal amino acid mutations and human brain endothelial cells is not affected. Mutant 1 and mutant 2 are functional mutants of human H-ferritin, the Fe storage function thereof is influenced by specific internal amino acid mutations. But the specific binding between these mutants and human brain endothelial cells is not affected.

Figure 11:
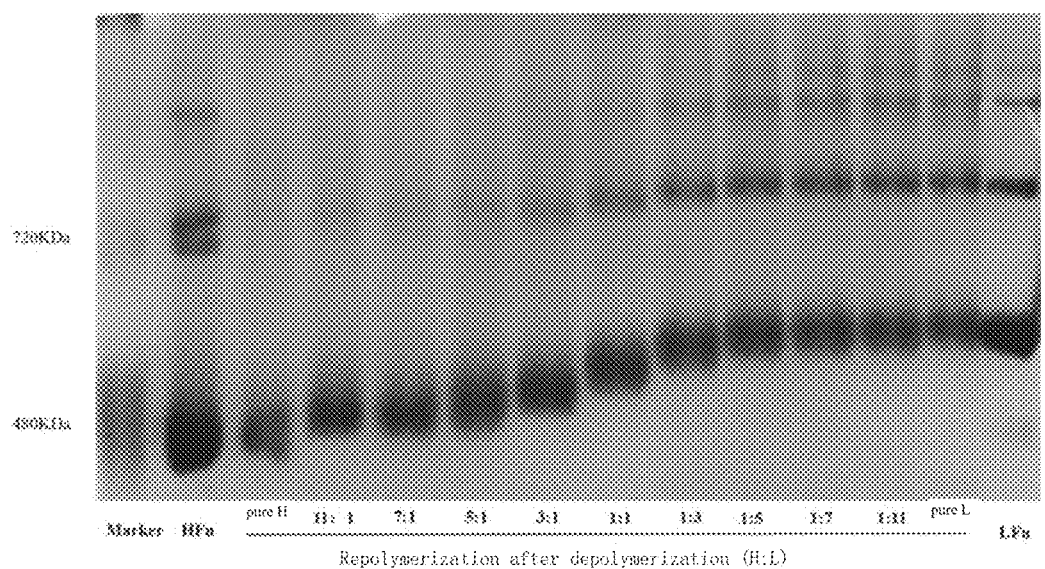

FIG. 11 shows the result of determination of purity of a hybrid-protein by Native PAGE.

Figure 12:
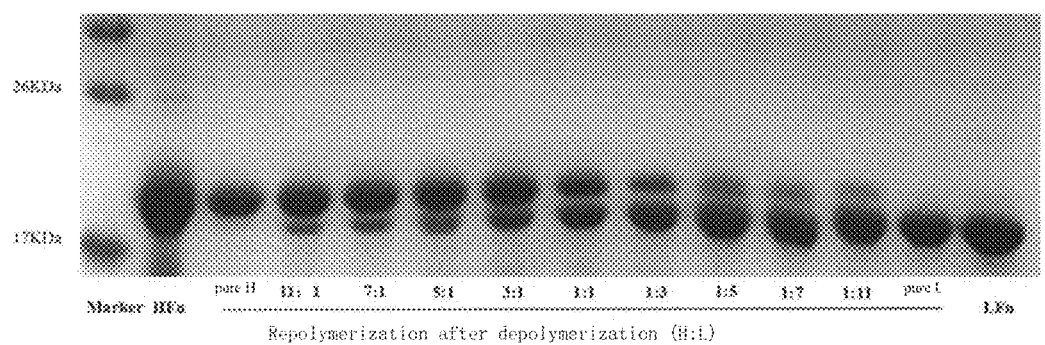

FIG. 12 shows the result of determination of the ratio of subunits of the hybrid-protein by SDS PAGE.

Figure 13:
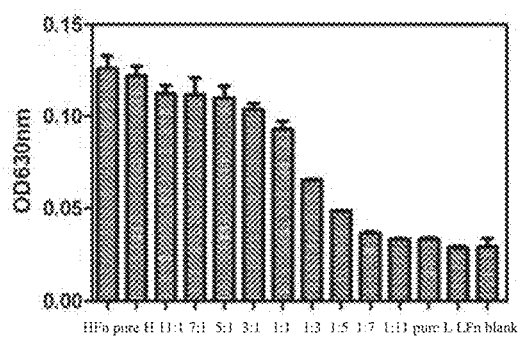
Figure 13:
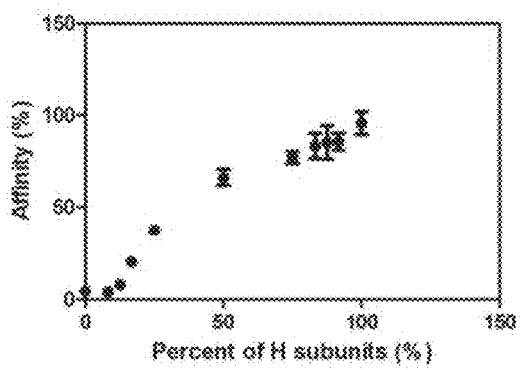

FIG. 13 shows the result of determination of affinity between the hybrid-protein and TfR1 by ELISA. FIGS. A and B respectively indicate $OD_{630nm}$ data and affinity data.

Figure 14:
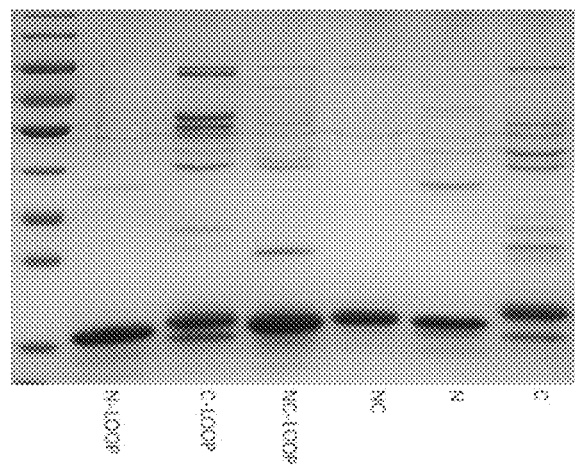

FIG. 14 shows a 12% SDS PAGE electrophoretic result of expression products of 6 modified proteins, e.g., C-terminal modified, N-terminal modified, etc.

Figure 15:
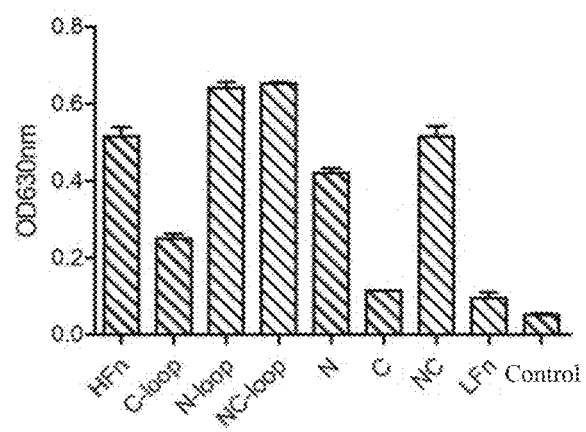

FIG. 15 shows the result of affinity between each of the 6 modified proteins and TfR1 measured by ELISA.

FIG. 16 shows residues on HFn playing an important role to the receptor TfR1 binding, wherein Figs. A and B are locations of the residues playing an important role from different visual angles (mainly located near the triad axis of ferritin, N-terminal of the structure); residues as shown in a colorful cartoon region are located in the triad axis region of a crystal structure of LFn proteins without TfR1 binding ability; residues as shown in a blue stick-shaped region are residues playing an important role to the receptor TfR1 binding, and these residues are located on the outer surface of the protein.

FIG. 17 shows composition of the amino acid sequence of a chimeric human ferritin, wherein black residues are from LFn, belonging to the frame sequences, as shown in the colorful cartoon region of the figure above; while underlined portions are residues playing an important role to the receptor TfR1 binding, as shown in the blue stick-shaped region of the figure above.

DETAILED DESCRIPTION OF THE INVENTION

Definition

Human H-ferritin refers to a ferritin which is formed by self-assemble of H subunits of human ferritin.

Human L-ferritin refers to a ferritin which is formed by self-assemble of L subunits of human ferritin.

Hybrid human ferritin refers to a ferritin which is formed by self-assemble of H subunits and L subunits of human ferritin, with an H/L subunit ratio different from that of natural human ferritin, for example, the H/L subunit ratio is 1:23~23:1. In some embodiments, the H/L subunit ratio is 1:5~15:1. In some embodiments, the H/L subunit ratio is 1:3~11:1. In some embodiments, the H/L subunit ratio is 1:1~5:1. In some embodiments, the H/L subunit ratio is 1:1~3:1. In some embodiments, the H/L subunit ratio is 15:1~3:1. And in some embodiments, the H/L subunit ratio is 11:1~3:1.

H/L functional region replacement refers that a region in H-ferritin responsible for binding with the receptor TfR1 is replaced to a L-ferritin, namely, the functional region of H-ferritin is transplanted onto L-ferritin to achieve the function of H-ferritin.

Cage protein: a globular protein formed by protein subunits in a certain spatial symmetrical structure is called a cage protein. In some embodiments of the invention, the cage protein refers to a cage protein self-assembled by H subunits of human ferritin, and the number of H subunits of human ferritin thereof has no specific limitation, provided that they can self-assemble under a certain condition into the cage protein. In some embodiments, the number of H subunits of human ferritin as comprised may be 3-30, preferably 6-28, more preferably 8-26, 10-26, 12-26, 14-26, 16-26, 18-26, 20-26, 22-26, most preferably 24, and any natural number within the range. In some embodiments, as mentioned above, the cage protein is a hybrid protein formed by H subunits and L subunits of human ferritin, with a ratio different from that of a natural human ferritin, and maintains the bioactivity of human ferritin, e.g., the ability to cross BBB.

There is no specific limitation to the drug than can be loaded in the cage protein of the invention, as long as the drug does not affect the structure and property of the cage protein, and can be accommodated in the cavity of the cage protein. In some embodiments, the drug is selected from alkylating agents, e.g., nitrosoureas; Pt types, e.g., cisplatin and carboplatin and derivatives thereof; antimetabolites, e.g., thymidylate synthase inhibitors; antibiotics, e.g., doxorubicin, daunomycin, daunorubicin; natural extracts, e.g., plant alkaloids (vinblastine); hormones, e.g., anti-estrogens (tamoxifen); radiopharmaceuticals, e.g., $^{64}$Cu, $^{235}$U; neurotransmitters, e.g., carbachol, atropine, scopolamine, dopamine and derivatives thereof; dopamine receptor agonists, e.g., bromocriptine, pergolide, apomorphine and other ergot alkaloid derivatives and non-ergot alkaloid derivatives; central nervous anticholinergic agents, e.g., trihexyphenidyl, benzatropine and procyclidine; cholinoceptor agonists, e.g., muscarine, pilocarpine; γ-secretase inhibitors, e.g., difluoro ketones; antioxidants, e.g., melatonin; anesthetics, e.g., anthryl amine, and the like. Accordingly, the disease that can be treated or prevented by the drug carrier of the invention is only limited by the drug loaded therein, namely, the disease that can be treated or prevented by the drug carrier of the invention depends on what are treated or prevented by the drug loaded therein. In some embodiments of the invention, the diseases capable of being treated or prevented are selected from a brain tumor, Alzheimer disease, Parkinson's disease, stroke, epilepsy, Huntington's disease and amyotrophic lateral sclerosis. The drug may be used for treating human malignant tumors and cancers, preferably for treating colorectal cancer, lung cancer, breast cancer, ovarian cancer, melanoma, stomach cancer, pancreatic cancer, bladder cancer, kidney cancer, prostatic cancer and other various hematologic malignancies, e.g., Hodgkin's disease, Non-Hodgkin's lymphoma, leukemia, etc.

Reconstitution (reconstitute) refers to a process that different gene sequences are recombined by means of genetic engineering, and the recombinant protein is expressed by a protein expression system. In the invention, the reconstitution relates to the fusion of the amino acid sequences as shown in SEQ ID NO: 1-3, 20-25 to scaffold sequences, thus allowing the amino acid sequences as shown in SEQ ID NO: 1-3, 20-25 presented on the surface of the cage protein formed and allowing the scaffold sequences located inside the cage protein. A scaffold sequence refers to an amino acid sequence which is fused to the sequences as shown in e.g., SEQ ID NO: 1-3, 20-25 and presents them on the outer surface of the cage protein. In some embodiments, the amino acid sequences as shown in SEQ ID NO: 1-3, 20-25 are segmented by the scaffold sequences. In some embodiments, there are 1-5 amino acid residues, preferably, 1, 2 or 3 amino acid residues, preferably, 1 amino acid residue, before N-terminal of SEQ ID NO: 1, preferably, the amino acid residue is M. In some embodiments, the scaffold sequence has a sequence as shown in SEQ ID NO: 4-6, 26-31. In some embodiments, the sequences of a recombinant obtained by reconstitution are fused according to the following way: SEQ ID NO: 1-SEQ ID NO: 4-SEQ ID NO: 2-SEQ ID NO: 5-SEQ ID NO: 3-SEQ ID NO: 6. In some embodiments, the sequence of the recombinant obtained by reconstitution is as shown in SEQ ID NO: 7 or 19. Those skilled in the art know the method to present the amino acid sequences as shown in SEQ ID NO: 1-3, 20-25 on the outer surface of the self-assembled cage protein, e.g., by molecular cloning (Molecular Cloning 4th: A Laboratory Manual, Cold Spring Harbor Laboratory Press). The scaffold sequences are located inside the cage protein, which can comprise a plurality of amino acid mutations, e.g., 1, 2, 3, 4, 5 or more amino acid substitution, deletion and/or addition, without influencing the binding between the cage protein and TfR1 and transporting. In some embodiments, the amino acid sequences as shown in SEQ ID NO: 1-3, 20-25 may have 1, 2, 3, 4, 5 or more amino acid substitution, deletion and/or addition, without affecting their presentation on the outer surface of the self-assembled cage protein as well as the binding between the cage protein and TfR1 and transporting. In some embodiments, a mutant of the sequence as shown in SEQ ID NO: 1-3, 20-25 has the same function with SEQ ID NO: 1-3, 20-25, the sequence of the mutant has at least 80%, e.g., 80%, 85%, 90%, 95%, 96%, 97%, 98%, 99% or higher sequence identity to the sequence as shown in SEQ ID NO: 1-3, 20-25. In some embodiments, the scaffold sequence above is a sequence of human L subunit located inside the cage protein and corresponding to human H subunits, e.g., sequences of amino acid positions 1-9, 14-18, 22-76, 80-85, 88-90, 103-115, 123-152, 158-175 on L subunits of human ferritin (SEQ ID No. 12) or a sequence as shown in SEQ ID No. 26-31.

A functional fragment of human H-ferritin refers to a protein sequence which is presented on the surface of human H-ferritin and plays a decisive role to receptor binding. In some embodiments, the sequence of the functional fragment is as shown in SEQ ID NO: 1-3, 20-25. Some embodiments of the invention further relate to a polynucleotide and a vector encoding the functional fragment. A polynucleotide encoding the sequence fragment is called a functional polynucleotide. A recombinant expression vector comprising the polynucleotide is a functional fragment expression vector.

A mutant of human H-ferritin refers to a product having amino acid residue mutation as compared with natural human H-ferritin. In some embodiments, the mutation is located inside the human H-ferritin (namely, the cage protein), namely, the mutation is not a mutation presented on the outer surface of human H-ferritin. Same as human H-ferritin, the mutant can recognize its natural receptor TfR1 and can cross BBB by TfR1 transporting. In some embodiments, compared with natural human H-ferritin, the mutant may have one or more amino acid mutations, e.g., substitution, deletion and/or addition of 1, 2, 3, 4, 5, 6, 7, 8, 9, 10, 11, 12, 13, 14, 15, 20, 25 or more amino acid residues, without influencing the binding between the cage protein and TfR1 and transporting. In some embodiments, the mutant has at least 80%, e.g., 80%, 85%, 90%, 95%, 96%, 97%, 98%, 99% or higher sequence identity to natural human H-ferritin, without influencing the binding between the cage protein and TfR1 and transporting.

Sequence identity refers to the percentage of residues of a polynucleotide or a polypeptide sequence mutant which are the same as the non-mutant sequence after sequence alignment and gap introduction (if necessary, to obtain maximum percentage identity). As length of sequences may be different, even a same number of amino acid nucleotide mutations, e.g., substitution, deletion and/or addition occur, the sequence identity caused thereby may be different, and, in most cases, the sequence identity obtained by computation is not an integer of percentage exactly, but a number containing decimals. Therefore, the percentage of the sequence identity above also includes the proximal percentage containing decimals obtained by corresponding actual computation.

In some embodiments, the mutation refers to conservative amino acid substitution. In some embodiments, conservative substitution may be defined by the substitution within amino acid categories in one or more of the three tables below:

Amino Acid Categories for Conservative Substitution:

TABLE 1

| | |
|---|---|
| Acidic residues | Asp (D) and Glu (E) |
| Alkaline residues | Lys (K), Arg (R) and His (H) |
| Uncharged hydrophilic residues | Ser (S), Thr (T), Asn (N) and Gln (Q) |
| Uncharged aliphatic residues | Cly (G), Ala (A), Val (V), Leu (L) and Ile (I) |
| Uncharged nonpolar residues | Cys (C), Met (M) and Pro (P) |
| Aromatic residues | Phe (F), Tyr (Y) and Trp (W) |

Alternative Conservative Substitutions:

TABLE 2

| | | | |
|---|---|---|---|
| 1 | A | S | T |
| 2 | D | E | |
| 3 | N | Q | |
| 4 | R | K | |
| 5 | I | L | M |
| 6 | F | Y | W |

Amino Acid Substitutions According to Physical and Functional Classification:

TABLE 3

| | |
|---|---|
| Residues containing an alcohol group | S and T |
| Aliphatic residues | I, L, V and M |
| Cycloalkenyl-related residues | F, H, W and Y |
| Hydrophobic residues | A, C, F, G, H, I, L, M, R, T, V, W and Y |
| Negatively-charged residues | D and E |
| Polar residues | C, D, E, H, K, N, Q, R, S and T |
| Positively-charged residues | H, K and R |
| Small residues | A, C, D, G, N, P, S, T and V |

TABLE 3-continued

| | |
|---|---|
| Tiny residues | A, G and S |
| Corner formation-involved residues | A, C, D, E, G, H, K, N, Q, R, S, P and T |
| Flexible residues | Q, T, K, S, G, P, D, E and R |

A more conservative substitution grouping includes: valine-leucine-isoleucine, phenylalanine-tyrosine, lysine-arginine, alanine-valine and asparagine-glutamine.

Other amino acid groupings further formulated by a principle described in Creighton, 1984, Proteins: Structure and Molecular Properties, Ver. 2, 1993, W. H. Freeman and Company may also be used.

By an extensive and thorough study, it has been found by the inventors that human H-ferritin can cross BBB via receptor TfR1-mediated transcytosis and can also target a brain tumor actively based on the preliminary work (Kelong Fan, et al and Xiyun Yan. Magnetoferritin nanoparticles for targeting and visualizing tumour tissues. Nature Nanotechnol. 7, 459-464 (2012); Minmin Liang, Kelong Fan, et al and Xiyun Yan. H-ferritin-nanocaged doxorubicin nanoparticles specifically target and kill tumors with a single-dose injection. Proc. Natl. Acad. Sci. USA 111(41): 14900-14905 (2014)) and a Chinese invention patent ZL201110122433.0 as well as a patent application 201410230829.0. On this basis, the invention is arrived at.

The full-length amino acid sequence of human H-ferritin is as shown in SEQ ID NO:10. In some embodiments, a functional fragment of human H-ferritin is used, wherein the functional fragment is effectively fused in the subunit thereof and self-assembled into a cage protein, and the sequence is presented on the outer surface. In some embodiments, the amino acid sequence of the functional fragment is as shown in SEQ ID NO: 1-3, 20-25. In some embodiments, all-heavy-chain human ferritin is modified in the invention to obtain a mutant of human H-ferritin, in which the amino acid sequence above is site-directed modified, without affecting its binding with the receptor and BBB crossing. In some embodiments, mutation sites of the mutant are located inside the cage protein as formed. In some embodiments, mutation sites of the mutant are located on the outer surface of the cage protein. In some embodiments, mutation sites of the mutant are located inside the cage protein and the outer surface thereof. In some embodiments, the sequence of the mutant is as shown in SEQ ID NO: 8 or SEQ ID NO: 9. In some embodiments, mutation sites of the mutant are located in the scaffold sequence. In some embodiments, the amino acid sequence of the scaffold sequence is as shown in SEQ ID No. 4-6, 26-31.

Hereby the invention is further described specifically with reference to detailed examples, and the following examples are only for describing the invention but not to limit the invention. It should be understood by those skilled in the art that any variation, modification or example implemented by directly employing equal conditions of the examples of the invention should be understood as within the scope of the invention.

Unless otherwise specified, the following experimental methods are conventional methods, and the experimental materials used can be obtained commercially.

EXAMPLES

Example 1 Human H-Ferritin Specifically Binds to Human Brain Endothelial Cells Via the Receptor TfR1

To study whether human H-ferritin specifically binds to human brain endothelial cells, human brain endothelial hCMEC/D3 cells (EMD Millipore Corporation: SCC066) are selected for this study. Firstly, the invention proves in vitro that the receptor TfR1 of H-ferritin is highly expressed on human BBB brain endothelial hCMEC/D3 cells. Then human BBB brain endothelial hCMEC/D3 cells are incubated with human H-ferritin labeled with fluorescent molecules, and the binding between human H-ferritin and tumor cells is tested by flow-cytometry and laser confocal microscopy.

Experimental methods are as follows:

a) Expression of TfR1 on Human Brain Endothelial Cells.

Figure 1:
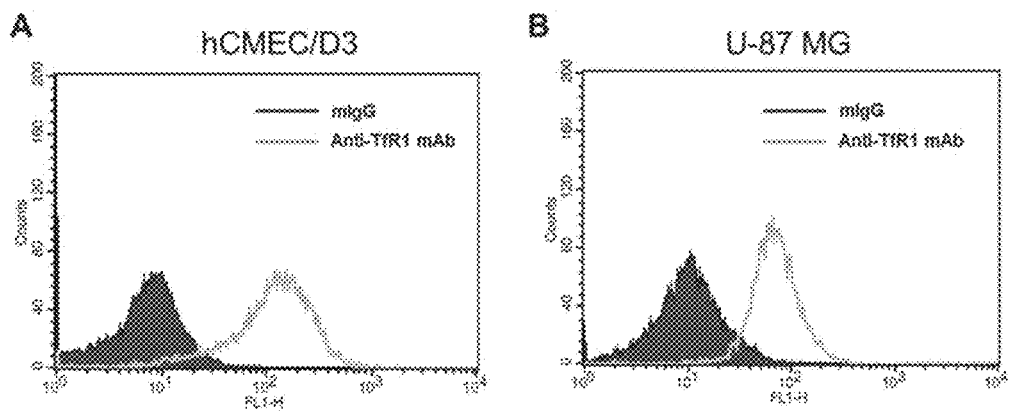
FIG. 1 shows that a receptor TfR1 of human H-ferritin is highly expressed by major constituents of human BBB-human brain endothelial cells hCMEC/D3 (A) and human glioma cells U-87 MG (B).

Human BBB brain endothelial hCMEC/D3 cells were cultured to about $1\times10^5$ (100×20 mm culture dish, Corning, USA). Culture conditions: the cells were cultured in EBM-2 medium (Gibco Life Technologies Inc., UK) containing growth factors and cortisol and supplemented with 2.5% (v/v) fetal bovine serum (Sigma-Aldrich) and penicillin (100 U/mL, Sigma-Aldrich) and streptomycin (100 g/mL, Sigma-Aldrich) at 37° C., 5% $CO_2$. After being digested with trypsin, the cells were washed with 0.3% (w/v) BSA/PBS (pH7.4) for three times, mouse anti-human TfR1 monoclonal antibodies (Santa Cruz, Clone M-A712) were added at a ratio of 1:200, and mouse mIgG was added to a control group for incubation 45 min at 4° C. The cells were washed with 0.3% BSA/PBS for three times, then goat anti-mouse IgG labeled with Alexa Fluor 488 (Thermo Fisher Scientific) was added at a ratio of 1:500 for incubation 45 min at 4° C. The cells were washed with 0.3% BSA/PBS for three times, finally resuspended in PBS (pH7.4). Fluorescence of the samples was tested by flow-cytometry (at a wavelength of 488 nm). The result is shown in FIG. 1A and indicates that the receptor TfR1 of H-ferritin is highly expressed on human BBB brain endothelial hCMEC/D3 cells.

b) Specific Binding Between Human H-Ferritin and Human Brain Endothelial Cells.

Figure 2:
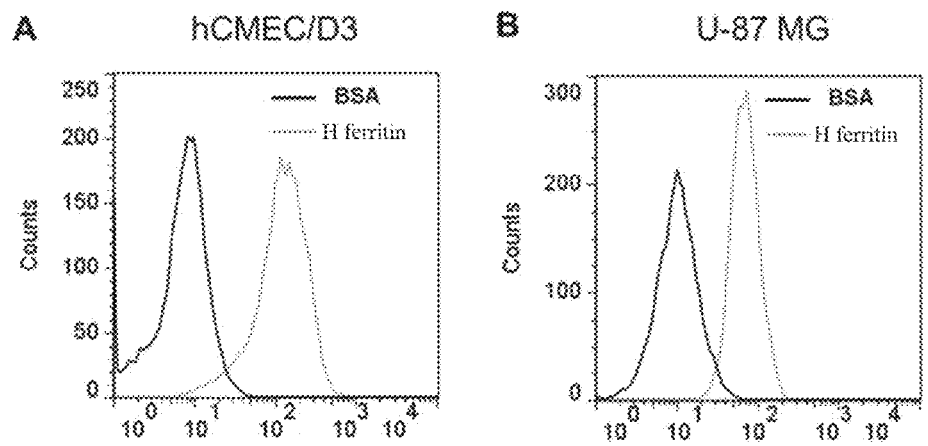
FIG. 2 shows that human H-ferritin specifically binds to human brain endothelial cells hCMEC/D3 (A) and glioma cells U-87 MG (B) via the receptor TfR1.

According to the labeling method provided in the instruction for use, NHS-activated FITC (purchased from Sigma) was labeled on the outer surface of human H-ferritin. The preparation method of human H-ferritin may refer to a patent of the applicant (patent No.: ZL201110122433.0, and the amino acid sequence may refer to NCBI accession number NP_002023.2). Human BBB brain endothelial hCMEC/D3 cells were cultured to about $1\times10^5$ (100×20 mm, dish Corning, USA) and digested with trypsin, then the cells were washed with 0.3% (w/v) BSA/PBS (pH7.4) for three times. 50 µg/ml FITC-labeled human H-ferritin was added, and FITC-labeled BSA was added in the control group for incubation for 45 min at 4° C. The cells were washed with 0.3% BSA/PBS for three times, finally resuspended in PBS (pH7.4). And fluorescence of the samples was tested by flow cytometry (at a wavelength of 488 nm). The result is shown in FIG. 2A, indicating that human H-ferritin can specifically, directly binds to human brain endothelial cells highly expressing TfR1. In combination with the preliminary results of the applicant (Kelong Fan, et al and Xiyun Yan. Magnetoferritin nanoparticles for targeting and visualizing tumour tissues. Nature Nanotechnol. 7, 459-464 (2012)), TfR1 is a major receptor of human H-ferritin for the binding with human cells. Thus it is found by the inventors that human H-ferritin can specifically bind to human BBB brain endothelial hCMEC/D3 cells via TfR1 binding.

Example 2 Subcellular Localization of Human H-Ferritin after Entering Human Brain Endothelial Cells A classic intracellular path of TfR1: after binding with a ligand, the receptor TfR1 mediates endocytosis to enter the endosome, and then enter the lysosome. To cross BBB, the first question to be answered is whether the ligand enters the lysosome after binding with TfR1. The invention proves for the first time that in human brain endothelial cells, most of H-ferritins exist in the endosome instead of being co-localized with the lysosome, which provides a support for crossing BBB from the aspect of intracellular localization.

Figure 3:
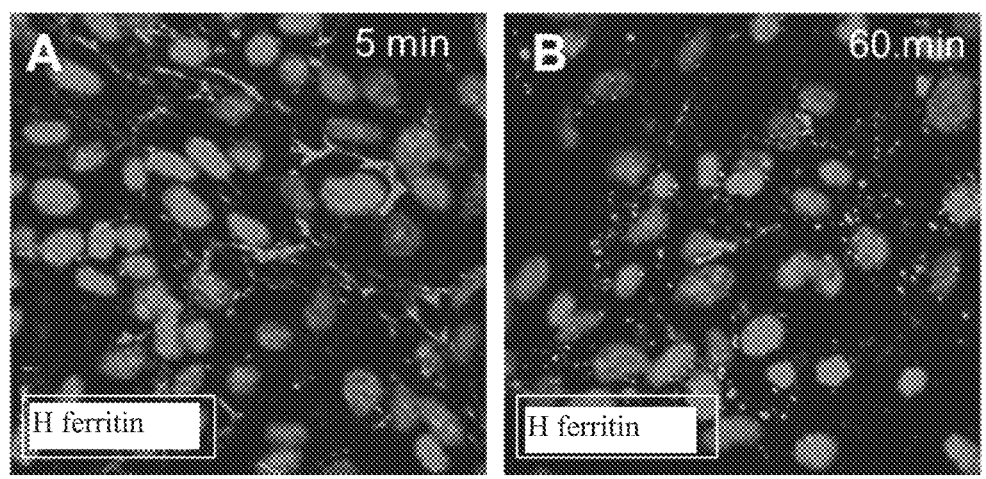
FIG. 3 shows that human H-ferritin may be effectively endocytosed by human brain endothelial cells hCMEC/D3. After binding with TfR1 highly expressed on brain endothelial cells, human H-ferritin is firstly localized on cytomembrane (A), and then effectively endocytosed inside the cells (B).

Detailed experimental methods are as follows:

a) Human H-Ferritins can be Effectively Endocytosed by Human BBB Brain Endothelial Cells Human BBB brain endothelial cells hCMEC/D3 slides (BD Biosciences) were placed in a 6-well plate (with well diameter of 34.8 mm, Corning, USA) for culturing above to a density of about 60%, then the experiment was conducted. 1 µM FITC-labeled H-ferritin above was added, and incubated respectively for 5 min and 6 min at 37° C. Then the cells were washed with 0.3% BSA/PBS for three times, and finally fixed with 4% paraformaldehyde. After being washed with PBS (pH7.4) for three times, cell nuclei were stained with DAPI (Roche Applied Science) 10 min at room temperature. After being washed by PBS for three times again, the slides were mounted with a mounting medium, and observed by laser confocal microscopy (Olympus FluoView FV-1000, Tokyo, Japan). The results are as shown in FIG. 3. FIG. 3A indicates that most of the FITC-labeled H-ferritins still bound with TfR1 on cytomembrane within a short period (5 min). FIG. 3B indicates that after being incubated for 60 min, most of the H-ferritins were present in brain endothelial cells in the form of endosome vesicles. Thus H-ferritins can be effectively absorbed and endocytosed by brain endothelial cells.

b) Co-Localization of Human H-Ferritins in Human BBB Brain Endothelial Cells.

Figure 4:
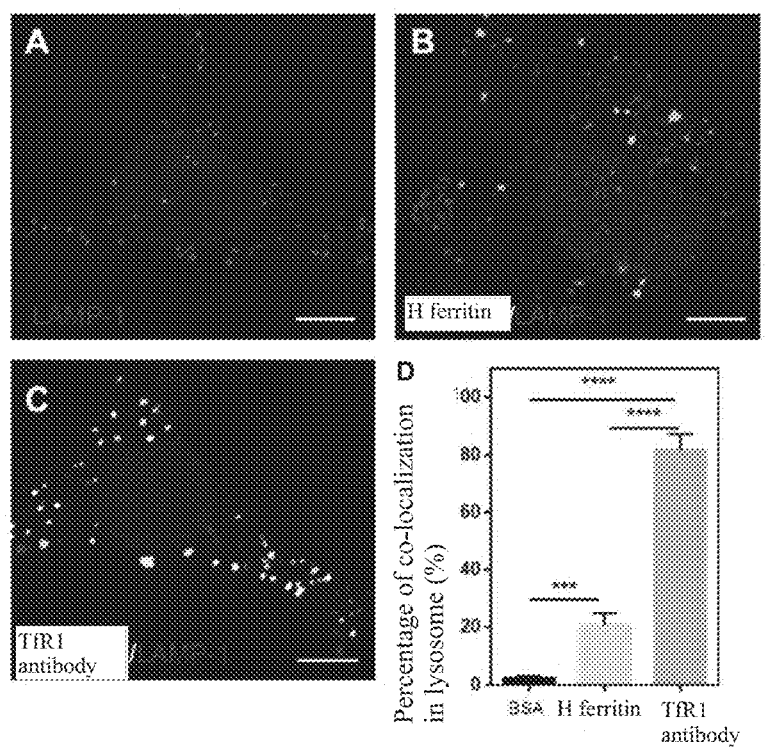
FIG. 4 shows the path of human H-ferritin in human brain endothelial cells hCMEC/D3. Mediated by TfR1, human H-ferritins are endocytosed after binding with brain endothelial cells, and then enter the endosomes. Afterwards, most of human H-ferritins still stay in the endosomes instead of entering lysosomes (LAW-1, a lysosome marker) (A, B). In contrast, majority of the anti-TfR1 antibodies enter lysosomes (C, D). The scale bar is 10 micrometers. *p<0.001; **p<0.0001.

Human BBB brain endothelial cells hCMEC/D3 slides (BD Biosciences) were placed in a 6-well plate for culturing to a density of about 60%, and then the experiment was conducted. 1 µM FITC-labeled H-ferritin was added, and Alexa Fluor 488-labeled mouse anti-human TfR1 monoclonal antibodies (1:200, Clone: M-A712, Santa Cruz) were added in the control group for incubation for 4 h in an incubator. The cells were fixed with 4% paraformaldehyde after being washed with PBS for three times. Then 0.1% Triton X-100 was used for cell permeabilization After being washed with PBS again, the cells were blocked in 5% goat serum (ZSGB-BIO) 30 min at room temperature, and then incubated in Alexa Fluor®555-labeled antibodies and lysosome marker molecules LAMP1 (1:200, clone H4A3; Invitrogen) for 1 h at 37° C. Finally, cell nuclei were stained with DAPI (1 µg/mL, Roche Applied Science) for 10 min at room temperature, observed under a laser scanning confocal microscope (Olympus FluoView FV-1000, Tokyo, Japan). The results are as shown in FIG. 4, the FITC-labeled H-ferritins and Alexa Fluor®488-labeled antibodies were green (white as shown in the figure), the lysosome marker molecules LAMP-1 were red (dark gray as shown in the figure), and if the lysosomes co-localized with the antibodies or ferritins, they showed bright white in the figure. By observing the behavior of HFn in the cells, it is found by the inventor that after binding with the receptor on BBB brain endothelial cell membrane, H-ferritins are transported to the endosome through endocytosis mediated by the receptor. Different from the previous results, most of the H-ferritins in brain endothelial cells do not enter the lysosome (FIGS. 4A and B, the white and dark gray regions did not basically co-localize, and there was no bright white point). Different from human H-ferritin, anti-TfR1 monoclonal antibodies are transported to the endosome after binding with the receptor on BBB brain endothelial cells, and finally almost all antibodies enter the lysosome (FIGS. 4C and D, almost all antibodies co-localized with the lysosome to form bright white points, and FIG. 4D is a quantitative analysis chart). These results provide a cellular/sub-cellular localization basis for H-ferritins to cross the blood brain barrier.

Figure 5:
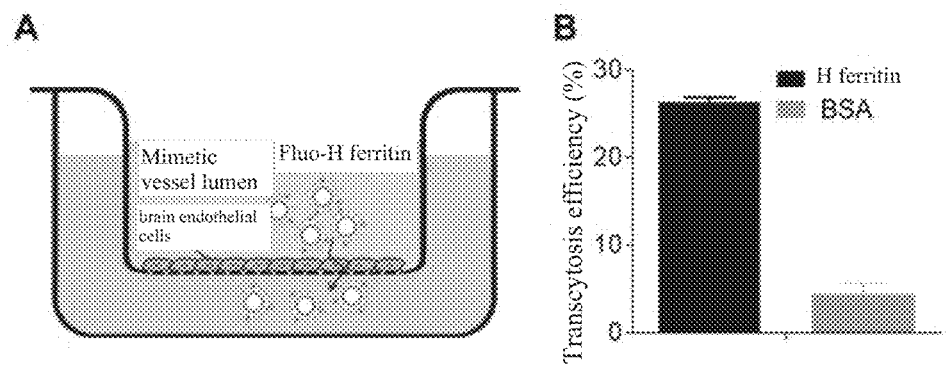
FIG. 5 shows a BBB model indicating that human H-ferritin can cross the blood brain barrier effectively via receptor TfR1-mediated transcytosis.

Example 3 Human H-Ferritin can Effectively Cross the Blood Brain Barrier Model a) Establishment of a BBB Model Human BBB brain endothelial cells hCMEC/D3 ($2\times10^4$/pore) were inoculated on a Transwell plate (3 μm well diameter, Corning, USA) pretreated with gelatin (10 μg/cm$^2$) (culture conditions are the same as that in Example 1). The cells were cultured at 37° C. under $CO_2$ in an incubator to confluence (2-3d). After the confluence state of hCMEC/D3 was observed by a microscope, medium (EBM-2 medium) was added to an upper chamber of the Transwell plate, resulting a more than 0.5 cm difference of liquid level between the upper and lower chamberst. If an obvious difference between the two chambers can be still observed after 4 h, it was regarded as completely confluent. The wells of Transwell without inoculated cells were used as a blank control. A BBB model was now established successfully (FIG. 5A).

b) Human H-Ferritins Cross the Blood Brain Barrier

Equal amount (50 μg/mL) of FITC-labeled H-ferritins and the control FITC-labeled BSA were dissolved in EBM-2 medium (Gibco Life Technologies Inc., UK). The original medium in the BBB model was discarded, and the EBM-2 medium containing equal amount of FITC-H ferritin and FITC-BSA was added to the upper chamber of the Transwell plate (simulating vessel lumen), then a blank EBM-2 medium was added to the lower chamber, allowing the liquid between the upper and lower chambers at a same level. The total volume (V) of the lower chamber was measured after being cultured for 6 h in a cell incubator. And then, 50 μL samples were respectively taken out of the lower chamber, and H-ferritin or BSA concentration (C) was measured by measuring fluorescence intensity (wavelength 488 nm). Afterwards, transcytosis efficiency was calculated according to the following formula: transcytosis efficiency %= $(C_{lower\ chamber} \times V_{lower\ chamber})/(C_{initial} \times V_{initial}) \times 100\%$. The result is as shown in FIG. 5B, H-ferritin can significantly cross the BBB model compared with BSA.

Example 4 Human H-Ferritin can Specifically Target Gliocytoma

After crossing the blood brain barrier, H-ferritin is capable of targeting brain tumors as its receptor TfR1 is highly expressed on various tumor cells. In the invention, gliocytoma cell line U87-MG (ATCC:HTB-14) was used by the inventor to test the targeting ability of H-ferritin to glioma. It has been found by the inventor that different from the behavior in brain endothelial cells, H-ferritin will be rapidly endocytosed to the lysosome after specifically binding to glioma via the receptor TfR1, thus achieving effective enrichment of H-ferritins in tumor cells. In a mouse glioma model, it has been found by the inventor that H-ferritin has good in-vivo tumor targeting ability to glioma.

Detailed experiments are as follows:

a) Expression of TfR1 on Human Glioma Cells.

Human glioma cells U87-MG were cultured to about $1\times10^5$ (culture conditions are as follows: the cells were cultured on a DMEM medium (Sigma-Aldrich) with 10% fetal bovine serum (Sigma-Aldrich), penicillin (100 U/mL, Sigma-Aldrich) and streptomycin (100 g/mL, Sigma-Aldrich) at 37° C., 5% $CO_2$), and digested with trypsin. The cells were washed with 0.3% BSA/PBS for three times. Mouse anti-human TfR1 monoclonal antibodies (Santa Cruz, Clone M-A712) were added at a ratio of 1:200, and mouse mIgG was added to a control group, incubated for 45 min at 4° C. The cells were washed with 0.3% BSA/PBS for three times, then goat anti-mouse IgG labeled with Alexa Fluor 488 (Thermo Fisher Scientific) was added at a ratio of 1:500, incubated for 45 min at 4° C. The cells were washed with 0.3% BSA/PBS for three times, finally resuspended in PBS (pH7.4), and fluorescence of the samples was measured by flow cytometry (wavelength 488 nm). The results are as shown in FIG. 1B. The H-ferritin receptor, TfR1, is highly expressed on human glioma U87-MG cells.

b) Specific Binding of Human H-Ferritin to Human Glioma Cells.

Human glioma U87-MG cells were cultured to about $1\times10^5$ and digested with trypsin. Then the cells were washed with 0.3% (w/v) BSA/PBS for three times. 50 μg/ml FITC-labeled human H-ferritin above was added, while FITC-labeled BSA was added to the control group, incubated for 45 min at 4° C. And then the cells were washed with 0.3% BSA/PBS for three times, finally resuspended in PBS. Fluorescence of the samples was measured by flow cytometry (wavelength 488). The results are as shown in FIG. 2B, which demonstrate that human H-ferritin can directly bind to human brain endothelial cells highly expressing TfR1 specifically.

c) Co-Localization of H-Ferritin in Human Glioma U87-MG Cells.

Human glioma U87-MG cells slides (BD Biosciences) were placed in a 6-well plate (with a well diameter of 34.8 mm, Corning, USA) for culturing to a density of about 60%. 1 μM FITC-labeled H-ferritin was added and incubated for 4 h in an incubator. The cells were fixed for 5 min with 4% paraformaldehyde after being washed with PBS (pH7.4) for three times. Then 0.1% Triton X-100 was used for cell permeabilization. After being washed with PBS again, the cells were blocked with 5% goat serum (ZSGB-BIO) for 30 min at room temperature, and then incubated with Alexa Fluor®555-labeled antibody and lysosome marker molecule LAMP1 (1:200, clone H4A3; Invitrogen) for 1 h at 37° C. Finally, cell nuclei were stained with DAPI (1 μg/mL, Roche Applied Science) for 10 min at room temperature. At last, the cells were observed with a laser scanning confocal microscope (Olympus FluoView FV-1000, Tokyo, Japan). The results are as shown in FIG. 6, FITC-labeled H-ferritins are green (white as shown in the figure), the lysosome marker LAMP-1 molecules are red (dark gray as shown in the figure). By observing the behavior of HFn in glioma cells, it has been found by the inventor that, different from the localization in BBB brain endothelial cells, upon binding to the receptor TfR1 on glioma U87-MG cells, H-ferritin is internalized through endocytosis mediated by the receptor and transported to the endosome, and finally, almost all antibodies enter the lysosome (FIGS. 6A and B, finally almost all white points in FIG. 6B co-localized with gray points). These experimental results indicate that after crossing the blood brain barrier, H-ferritin can target brain tumors specifically, and can achieve effective endocytosis and enrichment in brain tumor cells.

d) H-Ferritin can Specifically Target Tumor Lesions of a Mouse Glioma Model

A human TfR1 knock-in mouse (hTfR1-Balb/c) had been established. By means of transgenic technology, human TfR1 cDNA was inserted behind the first exon of mouse TfR1 in mouse embryonic stem cells, and initial portions of the exon 2 and intron of mouse TfR1 were knocked out, thus achieving replacement of mouse TfR1 with human TfR1, namely, obtaining a hTfR1 knock-in mouse. This mouse model was established by Nanjing Biomedical Research Institute of Nanjing University. A mouse glioma model was successfully established by the inventors via the steps of localizing with a brain localizer (Mouse™ Stereotaxic Instrument, Stoelting Co.), micro-injecting (10 μL) glioma cells (hTfR1-G422, human TfR1 stably-transfected cell line, purchased from MDL) with a microsyringe (10 μL, Hamilton) and then surgical suture of the hTfR1 knock-in mouse. 10 mg/Kg dose of Cy5.5 (GE Healthcare)-labeled H-ferritin and equivalent dose of BSA (Sigma) were administered via vein injection, and then live small animal imaging was conducted by a small animal imaging system IVIS (PerkinElmer). The results are as shown in FIG. 7, H-ferritin can specifically target glioma lesions, while BSA as a control has no targeting ability. These experimental results indicate that H-ferritin can effectively crossing the blood brain barrier and have a good targeting ability to glioma lesions in vivo.

Example 5 Human H-Ferritin Loaded with a Chemotherapeutic Agent Doxorubicin for Specifically Treating Mouse Glioma An animal therapy experiment was conducted by the inventor to glioma-bearing mice (same mice as in Example 4). In the experiment, glioma model mice (same mice as in Example 4) were divided into two groups, 5 mice for each group. And then glioma model mice were treated with doxorubicin (1 mg/Kg) respectively after tumor cell inoculation for 9d, 12d and 15d. Therapeutic results are as shown in FIG. 8 and indicate that doxorubicin-loaded H-ferritin (HFn-Dox) significantly improved survival rate of the glioma model mice (compared with Free-Dox, p<0.01), and greatly improved the survival period (30d), while the survival period of mice in Free-Dox group is 15d. These experimental results indicate that as a drug carrier, H-ferritin can cross the blood brain barrier and has significant therapeutic effects to glioma.

Example 6 Identification and Verification of Functional Fragments of Human H-Ferritin To further verify the functional fragments of human H-ferritin, by means of genetic engineering (Molecular Cloning 4th: A Laboratory Manual, Cold Spring Harbor Laboratory Press), the inventors replaced the amino acid sequences on the outer surface of human L-ferritin (which is self-assembled by L subunits of human ferritin with the amino acid sequence as shown in SEQ ID No.12 and NCBI accession number NP_002023.2, has similar space structure to human H-ferritin but is unable to cross the blood brain barrier) with SEQ ID NO: 1-3. The complete sequence of the subunit obtained is as follows:

(SEQ ID NO: 7)
M*TSQVRQNYHQDSEAAINRQINLELYASYVYLS*

M*SYYFDRDDVAL*EGVSHFFRELAEEKREGYERLLKMQ

NQR*GGRIFLQDIKKPDCDDWESGLNAMECALHLE*

-continued

K*NVNQSLLELHKLATDKNDP*HLCDFLETHFLDEEVK

LIKKM*GDHVTNLRKMGAPESGLAE*YLFERLTLKHD, in which the the core recognition sequences of human H-ferritin (numbered as SEQ ID NO: 1-3 sequentially) are shown in bold and Italic, and the support sequences of human L-ferritin (also called a scaffold sequence, except for M (Met) at position 1, the three sequences are sequentially numbered as SEQ ID NO: 4-6) are shown in normal letters. A fusion form of SEQ ID NO: 3, 2 and 1 is as shown in SEQ ID NO: 11. The protein as shown in SEQ ID NO: 7 is called chimeric human H-ferritin.

By recombinant expression and purification (expression and purification methods are referring to the inventor's patent: ZL201110122433.0), the inventor investigated the ability of chimeric human H-ferritin to cross the blood brain barrier. Detailed examples are as follows:

The experiments for specific binding between chimeric human H-ferritin and human brain endothelial cells were conducted according to Example 1b. The results are as shown in FIG. 9A. Human L-ferritin does not bind with human brain endothelial cells for lacking interaction with TfR1.

The experiments for the endocytosis of chimeric human H-ferritin by human brain endothelial cells and its sublocalization in the cells were conducted according to Example 2. The results are as shown in FIG. 9B, the FITC-labeled chimeric human H-ferritin showed white and the lysosome showed gray in the figure. Most of the chimeric human H-ferritins did not co-localize with the lysosome. It was clear for distinction.

The efficiency of chimeric human H-ferritin for crossing the in-vitro BBB model was determined according to Example 3. The results are as shown in FIG. 9 C. Chimeric human H-ferritin can significantly cross the blood brain barrier relative to L-ferritin.

It can be seen from these results that SEQ ID NO: 1-3 are essential functional regions for human H-ferritin to identify TfR1 and to cross BBB, and it is feasible to present them on the surface of a cage protein.

A crystal structure of HFn protein was further obtained in the invention, as shown in FIG. 16. FIG. 16 indicates residues on HFn playing important role in binding receptor TfR1. FIGS. 16A and B show the locations of the important residues from different visual directions (mainly located near the triad axis of ferritin, N-terminal of the structure). Residues as shown in colorful cartoon are located in the triad axis region of a crystal structure of LFn proteins without TfR1 binding ability, residues as shown in blue stick-shape are residues playing an important role in binding receptor TfR1, and these residues are located on the outer surface of the protein. FIG. 17 indicates the amino acid sequence (SEQ ID No.19) of another chimeric human ferritin of the invention, where black residues are derived from LFn proteins, belonging to frame sequences (scaffold sequences) as shown in colorful cartoon in the upper panel; while underlined portions are residues playing an important role in binding receptor TfR1, as shown in blue stick-shape in the upper panel. Sequences of the important residues above are respectively as shown in SEQ ID No. 20~25, and the scaffold sequences are as shown in SEQ ID No.26~31.

Example 7 Internal Mutations of Human H-Ferritin do not Affect its Ability of Targeting Brain Endothelial Cells To further verify whether the functional fragments of human H-ferritin are located on the outer surface and thus functions thereof are not affected by internal mutations, mutant 1 (SEQ ID NO: 8) and mutant 2 (SEQ ID NO: 9) were constructed respectively by the inventor via implementing mutations to the internal amino acids of human H-ferritin by means of genetic engineering (Molecular Cloning 4th: A Laboratory Manual, Cold Spring Harbor Laboratory Press). Mutant 1 comprised a site-directed mutation within the active sites locate internally in human H-ferritin, namely, 63E was mutated into 63K and 66H was mutated into 66G; mutant 2 comprised a site-directed mutation within the hydrophilic channel of human H-ferritin, namely, 131D was mutated into 131A and 134E was mutated into 134A. The two mutants are functional mutants, playing a decisive role to physiological functions of human H-ferritin, but the mutations are not presented on the outer surface of the cage protein formed. To verify that the ability of human H-ferritin to cross BBB is determined by functional sequences on the outer surface of the cage protein but not affected by the internal structure, the inventor investigated influences of mutant 1 and mutant 2 on specific binding of human brain endothelial cells.

The specific binding with human brain endothelial cells is tested according to Example 1b. The results are as shown in FIG. 10. There is no obvious difference between mutant 1, mutant 2 and human H-Ferritin in specific binding with human brain endothelial cells. This indicates that the internal protein structure of the cage protein only plays a role for supporting, and the sequences responsible for ability of crossing BBB are the functional sequences located on the outer surface of human H-ferritin.

Example 8 Construction of HFn-LFn Hybrid and Determination of Affinity

Experimental Materials:

HFn: prepared by the method of Example 1. The initial concentration is 1.1 mg/ml and concentrated to 5.7 mg/ml by a 100K ultrafiltration tube. (Buffer solution: 1×TBS, 20 mM Tris-HCl+150 mM NaCl pH8.0)

LFn: L-ferritin has an amino acid sequence referring to NCBI accession number NP_000137.2, was prepared by genetic engineering, using an expression vector pET30a and an expression strain *Escherichia coli* BL21 (conducted by a conventional method). Purification: 75° C. 20 min+QFF self-filled column (prefilled column: GE Healthcare; XK 26/20 column. Filler: GE Healthcare; 17-051001)+Hitrap 16/600 Superdex 200 pg molecular sieve purification. Protein concentration was quantified by a BCA kit (Thermo scientific; 23250) as 4.8 mg/ml. (buffer solution: 1×TBS, 20 mM Tris-Hcl+150 mM NaCl pH8.0)

Experimental Steps:

1. Mixing: HFn and LFn were mixed in a 20 mM Tris pH 8.2 solution according to a ratio purified H, 11:1, 7:1, 5:1, 3:1, 1:1, 1:3, 1:5, 1:7, 1:11, purified L, to obtained a protein concentration of 1 mg/ml after mixing (namely, the combined molar concentration of H and L subunits was about 48 uM).

2. Depolymerization: 5 ml mixed sample above were taken and adjusted to pH3.0 using 0.2M HCl, and then 6.7 g Gdn-HCl (guanidine hydrochloride) (about 7M after being dissolved) were added to the solution, the sample solution (final volume is about 10 ml) after being mixed was placed in a mixer (Kylin-Bell Lab Instruments Co., Ltd; WH-986), incubated for 2 h at 37° C.

3. Repolymerization: the incubated sample above was purified by a Hitrap 26/10 desalination column to remove Gdn-HCl, thus achieving protein repolymerization (final buffer solution: 1×TBS, 20 mM Tris-Hcl+150 mM NaCl pH8.0).

4. Measurement of protein concentration: protein concentration of the sample was measured by a BCA kit.

5. Identification of purity of the hybrid protein: the hybridized sample was characterized by 4% Native-PAGE to determine the purity and distribution of the hybrid proteins in the sample.

6. Identification of ratio of subunits in the hybrid protein: the hybrid with good purity was characterized by 12% SDS-PAGE to determine the ratio of subunits in the hybrid.

7. Identification of affinity between the hybrid and TFR1: the affinity between the synthesized hybrid above and TFR1 was determined by ELISA. Steps are briefly described as follows: ① The hybridized sample was diluted to 40 ug/ml by an antigen-coated solution (0.15 M $Na_2CO_3$, 0.35 M $NaHCO_3$, 0.03M $NaN_3$), and added to an ELISA plate at 100 ul/well, incubated overnight at 4° C. ② The sample was blocked by 5% skim milk (1×PBS diluted), 300 ul/well, treated in a wet box for 2 h at 37° C. ③ The sample was incubated with 2 ug/ml TFR1 (Sino Biological Inc.; 11020-MM02) (diluted by a protein stabilizer (InnoReagents; PR-SS-002)), 100 ul/well, treated in a wet box for 2 h at 37° C. ④ The sample was incubated with 1 ug/ml anti-TFR1 primary antibodies (mouse, Sino Biological Inc.; diluted by a protein stabilizer 11020-MM02), 100 ul/well, treated in a wet box for 2 h at 37° C. ⑤ The sample was incubated with anti-mouse secondary antibodies (anti-mouse IgG: (GE Healthcare; NA931V) (diluted by a HRP coupling stabilizer to 1:5000), 100 ul/well, treated in a wet box for 2 h at 37° C. ⑥ TMB one-step developing solution (InnoReagentsl TMB-S-004) was added at 100 ul/well for developing, then absorbance values were measured immediately at 630 nm, 1 time/min for 30 min. Note: the sample should be washed with 1×PBST for 3 times and the plate should be washed with 1×PBS for 2 times between steps.

Experimental Results and Discussion:

1. The results for identification of purity of the hybrid protein-Native PAGE are as shown in FIG. 11. It can be seen from FIG. 11 that various hybrids of different ratios are proportionally distributed between the unprocessed HFn and LFn, indicating a success of the hybrid construction. There is not a band for homopolymer, indicating that H and L subunits, when co-exist, are more inclined to form H/L dimers or polymers instead of H/H or L/L dimers or polymers. Hybrid bands are more compact and not distributed scatteredly, indicating that the hybrids exist mainly according to a predetermined ratio instead of a combination of various hybrid proteins with different H/L ratios, which further indicating that during the repolymerization, H and L will hybridize mutually as much as possible instead of hybridize randomly, thus forming hybrids with a single fixed ratio. In addition, after repolymerization, electrophoretic mobility of the purified H repolymerization samples is the same as the unprocessed HFn, and electrophoretic mobility of the purified L repolymerization samples is the same as the unprocessed LFn, indicating that the denaturalization-renaturation process does not affect the overall structure of the protein.

2. The results of identification of ratio of subunits in the hybrid protein-SDS PAGE are as shown in FIG. 12. It can be seen from FIG. 12 that the ratio of subunits in the hybrid is the same as the initial ratio, indicating a success of hybrid construction.

3. The results of identification of affinity between the hybrid and TfFR1-ELISA are as shown in FIGS. 13A and B.

It can be seen from FIG. 13 that with the increase of the percentage of H subunits in the hybrid, the affinity between the hybrid and TfR1 increased accordingly and showed a non-linear trend, indicating that the affinity between the hybrid and TfR1 does not depend on the percentage of H subunits only. When the H and L subunits ratio increased from 0 to 1:7, the hybrid had little affinity to TfR1. When the H and L subunits ratio increased from 1:5 to 1:1, there was an obvious increase in the affinity between the hybrid and TfR1. And When the H and L subunits ratio increased from 3:1 to purified H, a higher affinity between the hybrid and TfR1 was observed without a sharp rise. It is speculated that besides the ratio of H subunits in the hybrid, the specific combination manner between subunits (H/H dimer) may play an important role in binding with TfR1.

Example 9 Exchange of H/L Functional Regions and Affinity Measurement

Human H-ferritin (HFn) and L-ferritin (LFn) share a rather high homology on the primary sequences, although the latter lacks the ability to bind with the receptor TfR1. In this example, the inventor tried to replace some sequences of LFn with the corresponding sequences of HFn by recombinant DNA technology, so as to obtain a series of recombinant chimeric proteins after expression and purification in *Escherichia coli*, and then regions on HFn that may interact with receptor TfR1 were analyzed by testing the affinity of these proteins to receptor TfR1. The ELISA results of affinity testing indicate that N-terminal of HFn may involve in the interaction with the receptor TfR1, and meanwhile, loop regions also contribute to the interaction to a certain extent.

1. Plasmid Transformation 1.1 6 tubes of *Escherichia coli* BL21 competence cells were taken and 1 μL (100 ng/μL) plasmids N-loop-PET22b, C-loop-PET22b, NC-loop-PET22b, N-PET22b, C-PET22b and NC-PET22b (obtained by subcloning a N-loop as shown in SEQ ID No. 13, a C-loop as shown in SEQ ID NO. 14, a NC-loop as shown in SEQ ID No. 15, a N-terminal as shown in SEQ ID No. 16, a C-terminal as shown in SEQ ID No. 17 and a NC-fusion sequence as shown in SEQ ID No. 18 into PET22b via restriction enzymes NdeI and BamH I, the nucleotide sequences were optimized according to the codon preference of *Escherichia coli*) were respectively added for processing in ice for 0.5 h.

```
N-loop:
                                        (SEQ ID No. 13)
MSSQIRQNYHQDSEAAVNRQINLYLQASYTYLSLGFYFDRDDVALEGV
SHFFRELAEEKREGYERLLKMQNQRGGRIFLQDIKKPDCDEWGKTPDA
MKAAMALEKKLNQALLDLHKLATDKNDPHLCDFLETHFLDEEVKLIKK
MGDHLTNLHRLGGPEAGLGEYLFERLTLKHD C-loop
                                        (SEQ ID No. 14)
MSSQIRQNYSTDVEAAVNSLVNLYLQASYTYLSLGFYFDRDDVALEGV
SHFFRELAEEKREGYERLLKMQNQRGGRALFQDIKKPDCDEWESGLNA
MECALHLEKKLNQALLDLHALGSARTDPHLCDFLETHFLDEEVKLIKK
MGDHLTNLRKMGAPEAGLGEYLFERLTLKHD
```

-continued

```
NC-loop
                                        (SEQ ID No. 15)
MSSQIRQNYHQDSEAAVNRQINLYLQASYTYLSLGFYFDRDDVALEGV
SHFFRELAEEKREGYERLLKMQNQRGGRIFLQDIKKPDCDEWESGLNA
MECALHLEKKLNQALLDLHKLATDKNDPHLCDFLETHFLDEEVKLIKK
MGDHLTNLRKMGAPEAGLGEYLFERLTLKHD N terminal
                                        (SEQ ID No. 16)
MSSQIRQNYHQDSEAAVNRQINLYLQASYTYLSLGFYFDRDDVALEGV
SHFFRELAEEKREGYERLLKMQNQRGGRIFLQDIKKPAEDEWGKTPDA
MKAAMALEKKLNQALLDLHKLATDKNDPHLCDFLETHFLDEEVKLIKK
MGDHLTNLHRLGGPEAGLGEYLFERLTLKHD C terminal
                                        (SEQ ID No. 17)
MSSQIRQNYSTDVEAAVNSLVNLYLQASYTYLSLGFYFDRDDVALEGV
SHFFRELAEEKREGYERLLKMQNQRGGRALFQDIKKPAEDEWESGLNA
MECALHLEKKLNQALLDLHALGSARTDPHLCDFLETHFLDEEVKLIKK
MGDHLTNLRKMGAPEAGLGEYLFERLTLKHD NC fusion
                                        (SEQ ID No. 18)
MSSQIRQNYHQDSEAAVNRQINLYLQASYTYLSLGFYFDRDDVALEGV
SHFFRELAEEKREGYERLLKMQNQRGGRIFLQDIKKPAEDEWESGLNA
MECALHLEKKLNQALLDLHKLATDKNDPHLCDFLETHFLDEEVKLIKK
MGDHLTNLRKM GAPEAGLGEYLFERLTLKHD
```

1.2 The cell were heat shocked for 85 s at 42° C., placed in ice bath for 2 min.

1.3 500 μL LB medium was added to the tubes, cultured with shaking at 220 rpm for 50 min at 37° C., allowing *Escherichia coli* cells to recover a normal growth.

1.4 The cells were plated on LB plates (containing 0.1 mg/mL ampicillin), cultured for 1 h in an incubator at 37° C., and then the plates were placed up-side-down and cultured overnight.

2. Protein Induction Expression 2.1 A single colony was picked from each plate and inoculated respectively in 6 mL medium containing 0.1 mg/mL ampicillin, cultured with 220 rpm shaking for 12-14 h at 37° C.

2.2 750 μL culture solution was transferred to 750 ml LB medium (containing 0.1 mg/mL ampicillin), cultured with 220 rpm shaking for 12-14 h at 37° C.

2.3 1 mM IPTG was added for induction for 6 h.

2.4 44000 rpm centrifugation was conducted for 30 min, and pellets were collected.

3. Bacterial Cell Disruption

The collected bacterial precipitates were resuspended in 30 mL 20 mM Tris-HCL pH 8.0. After mixing, the cells were disrupted by a high-pressure cell crusher (JNBIO; JN-3000) under the pressure of 1200 bar repeatedly for 4 times, then 12000 rpm centrifugation was conducted to the collected solution for 30 min at 4° C. to collect the supernate.

4. Thermoprecipitation

The supernate was divided into conical flasks, treated at 72° C. in a water bath for 15 min, where the conical flasks were constantly shaken to ensure that the solutions were heated evenly. After thermoprecipitation, the solutions were immediately placed on ice and then centrifuged after cooling for 10 min at 12000 rpm to collect the supernate, namely, a crude protein solution.

5. Sulfate Precipitate The crude protein solution obtained from the step above was quantified, and 53 g ammonium sulfates per 100 mL supernate were added, stirred in a refrigerator for 2 h at 4° C., centrifuged for 30 min at 12000 rpm at 4° C. to collect the pellets. The pellets were reconstituted in 30 mL 20 mM pH 8.2 Tris and centrifuged for 30 min at 12000 rpm at 4° C., then the supernate was filtrated with a 0.22 μm filter.

6. Desalination

Chromatographic column: HiPrep 26|10 Desalting desalination column

Column volume: 50 mL
Buffer solution: 20 mM Tris-HCl buffer solution (pH 8.0)
Flow rate: 10 mL/min The desalination column was equilibrated with the buffer solution. Samples were loaded after conductivity was entirely equilibrated, with a loading volume of 10 mL, and eluted with 1.5 CV (column volume) buffer solutions. Elutions were tested at $A_{280}$ and peaks were collected in 15 mL centrifugal tubes, 10 mL per tube.

7. Anion Exchange

Chromatographic column: QFastFlow self-filled column
Column volume: 35 mL
Buffer solution A: 20 mM Tris-HCl buffer solution (pH 8.0)
Buffer solution B: 20 mM Tris-HCl buffer solution (pH 8.0)
Flow rate: 5 mL/min The anion exchange column was equilibrated with the buffer solution A. Samples were loaded after conductivity was entirely equilibrated, with a loading volume: 50 mL and a flow rate: 1 mL/min. After loading, the column was washed with 2 CV buffer solution A, and 0%-100% linear elution was conducted with 15 CV buffer solution B. Peaks were tested by $A_{280}$ and collected in 15 mL centrifugal tubes, 10 mL per tube. Samples containing target proteins after anion exchange were ultrafiltrated and concentrated, then further purified by molecular sieve.

8. Molecular Sieve

Chromatographic column: HiLoad 16/60 Superdex 200 pg
Column volume: 120.637 mL
Buffer solution A: 20 mM Tris-HCl buffer solution (pH 8.0)
Flow rate: 1 mL/min The molecular sieve was equilibrated with the buffer solution A. Samples were loaded after conductivity was entirely equilibrated, with a loading volume: 2 mL and a flow rate: 1 mL/min. After loading, 1 CV buffer solution A was used for elution. Peaks were tested by $A_{280}$ and collected in 15 mL centrifugal tubes, 2 mL per tube.

9. Measurement of Protein Content by BCA

N-LOOP: 2.314 mg/mL
C-LOOP: 0.908 mg/mL
NC-LOOP: 2.347 mg/mL
N: 0.815 mg/mL
C: 0.832 mg/mL
NC: 1.792 mg/mL
(Concentration of purified protein as measured)

10. SDS-PAGE

12% SDS-PAGE was prepared and electrophoresis was conducted for 60 min at 26 mA. 5 μg of total protein content for each sample was boiled 10 min at 100° C. and loaded. The results are as shown in FIG. 14.

11. Measurement of Affinity of Each of the 6 Modified Proteins to TfR1 by ELISA.

The plate was coated with 20 μg/mL protein overnight at 4° C., blocked with 5% BSA for 2 h at 37° C.; incubated with 2 μg/mL TfR1 (human, as mentioned above) for 2 h at 37° C.; incubated with 1 μg/mL anti-TfR1 (mouse, Sino Biological Inc.; 11020-MM02) primary antibody for 2 h at 37° C.; incubated with HRP enzyme-labeled second antibody (anti-mouse IgG: (GE Healthcare; NA931V) 1: 5000) for 2 h at 37° C.; one-step developed with TMB. A microplate reader $OD_{630}$ was used for reading. The results are as shown in FIG. 15.

12. Conclusion

Based on results of SDS-PAGE and ELISA, data as shown in table 4 is obtained:

TABLE 4

| Protein name | ELISA value | Purity of target protein | Converted ELISA value |
|---|---|---|---|
| HFn | 0.95 | | 0.95 |
| N-loop | 1.17 | 77.1% | 1.52 |
| C-loop | 0.31 | 43.7% | 0.71 |
| NC-loop | 1.23 | 60.8% | 2.02 |
| N | 0.88 | 67.6% | 1.30 |
| C | 0.1 | 59.6% | 0.17 |
| NC | 1.03 | 90.2% | 1.14 |
| LFn | 0.09 | | 0.09 |

By comparing the converted ELISA values of N/C/NC/LFn, it can be found: the value of C-terminal is slightly higher than that of LFn, and thus C-terminal has relatively weak affinity to TfR1; and the value of N-terminal is higher, and thus N-terminal has a dominant impact on affinity to TfR1.

By comparing converted ELISA values of N-loop/C-loop/NC-loop, it can be found that affinity of N-loop is apparently higher than affinity of N-terminal, indicating that loop has a certain impact on affinity to TfR1; affinity of N-loop is higher than C-loop, indicating that N-terminal has a dominant impact on affinity to TfR1.

Therefore, the inventor holds that affinity to TfR1 is influenced by each region, and is influenced by N-terminal significantly and by the loop to a certain extent, and maximum affinity is achieved when the three regions are combined. This again verifies the effect of the functional fragments as obtained in Example 6.

REFERENCES

[1] CLOUGHESY T F, CAVENEE W K, MISCHEL P S. Glioblastoma: from molecular pathology to targeted treatment [J]. Annual review of pathology, 2014, 9: 1-25.

[2] STURM D, BENDER S, JONES D T, et al. Paediatric and adult glioblastoma: multiform (epi)genomic culprits emerge [J]. Nat Rev Cancer, 2014, 14(2): 92-107.

[3] CHANG L, SU J, JIA X, et al. Treating malignant glioma in Chinese patients: update on temozolomide [J]. OncoTargets and therapy, 2014, 7: 235-44.

[4] BALLABH P, BRAUN A, NEDERGAARD M. The blood-brain barrier: an overview: structure, regulation, and clinical implications [J]. Neurobiol Dis, 2004, 16(1): 1-13.

The invention claimed is:

1. A mutant human ferritin H subunit composition comprising SEQ ID NO: 7.

2. The mutant human ferritin H subunit composition of claim 1, wherein the composition further includes a drug.

3. The mutant human ferritin H subunit composition of claim 2, wherein the drug is a chemotherapeutic drug or a drug against neurodegenerative diseases.

4. The mutant human ferritin H subunit composition of claim 3, wherein the drug is selected from an alkylating agent, an antibiotic, a plant alkaloid, a radiopharmaceutical, a neurotransmitter, a dopamine receptor agonist, a central nervous anticholinergic agent, a cholinoceptor agonist, a γ-secretase inhibitor, an antioxidant, and an anesthetic.

5. The mutant human ferritin H subunit composition of claim 4, wherein the alkylating agent is selected from cisplatin, carboplatin, and derivatives thereof; the antibiotic is selected from doxorubicin, daunomycin, and daunorubicin; the plant alkaloid is vinblastine; the radiopharmaceutical is selected from $^{64}$Cu and $^{235}$U; the neurotransmitter is selected from carbachol, atropine, scopolamine, dopamine and derivatives thereof; the dopamine receptor agonist is selected from bromocriptine, pergolide, apomorphine, and other ergot alkaloid derivatives and non-ergot alkaloid derivatives; the central nervous anticholinergic agent is selected from trihexyphenidyl, benzatropine and procyclidine; the cholinoceptor agonist is selected from muscarine and pilocarpine; the γ-secretase inhibitor is a difluoro ketone; and the antioxidant is melatonin; the anesthetic is anthryl amine.

6. A pharmaceutical composition, comprising the mutant human ferritin H subunit composition of any of claims 1-5.

7. The pharmaceutical composition of claim 6, for treating a brain tumor.

* * * * *